United States Patent
Ruderman et al.

(10) Patent No.: US 7,647,234 B1
(45) Date of Patent: Jan. 12, 2010

(54) CARDIOVASCULAR HEALTHCARE MANAGEMENT SYSTEM AND METHOD

(75) Inventors: Frank R. Ruderman, San Carlos, CA (US); David T. Shewmake, San Francisco, CA (US)

(73) Assignee: Berkeley Heartlab, Inc., Burlingame, CA (US)

( * ) Notice: Subject to any disclaimer, the term of this patent is extended or adjusted under 35 U.S.C. 154(b) by 886 days.

(21) Appl. No.: 09/534,946

(22) Filed: Mar. 24, 2000

Related U.S. Application Data

(60) Provisional application No. 60/126,003, filed on Mar. 24, 1999, provisional application No. 60/168,354, filed on Dec. 1, 1999.

(51) Int. Cl.
G06Q 50/00 (2006.01)

(52) U.S. Cl. .............................. 705/2; 705/3; 600/300; 600/301; 706/924

(58) Field of Classification Search ............ None
See application file for complete search history.

(56) References Cited

U.S. PATENT DOCUMENTS

| | | | | |
|---|---|---|---|---|
| 5,583,758 A | * | 12/1996 | McIlroy et al. ................ 705/2 |
| 5,589,104 A | * | 12/1996 | Bambeck .................... 516/103 |
| 5,619,991 A | | 4/1997 | Sloan .......................... 600/300 |
| 5,704,366 A | | 1/1998 | Tacklind et al. ............ 600/529 |
| 5,711,297 A | | 1/1998 | Iliff ............................. 600/300 |
| 5,724,575 A | | 3/1998 | Hoover et al. ................ 707/10 |
| 5,724,580 A | * | 3/1998 | Levin et al. .............. 707/104.1 |
| 5,730,146 A | | 3/1998 | Itil et al. ...................... 600/545 |
| 5,746,204 A | | 5/1998 | Schauss ....................... 600/300 |
| 5,778,882 A | | 7/1998 | Raymond .................... 600/513 |
| 5,785,650 A | | 7/1998 | Akasaka ...................... 600/300 |
| 5,802,495 A | | 9/1998 | Goltra ........................... 705/3 |
| 5,823,949 A | | 10/1998 | Goltra ......................... 600/300 |
| 5,827,180 A | | 10/1998 | Goodman .................... 600/300 |
| 5,832,448 A | * | 11/1998 | Brown ............................ 705/2 |
| 5,868,669 A | | 2/1999 | Iliff ............................. 600/300 |
| 5,910,107 A | | 6/1999 | Iliff ............................. 600/300 |
| 5,911,132 A | | 6/1999 | Sloane ........................... 705/3 |
| 5,911,687 A | | 6/1999 | Sato et al. .................... 600/300 |

(Continued)

OTHER PUBLICATIONS

Telemedicine Resources: *Telemedicine: A Brief Overview*, Jun. 23, 1999.

(Continued)

*Primary Examiner*—Gerald J. O'Connor
*Assistant Examiner*—Lena Najarian
(74) *Attorney, Agent, or Firm*—McDonnell Boehnen Hulbert & Berghoff, LLP

(57) ABSTRACT

The disclosure relates to an interactive, web based cardiovascular healthcare management system which has an infomediary site with databases having information relating to cardiovascular disease risk factors such as age, blood pressure, LDL, HDL and subfractions thereof and cardiovascular disease management such as diet, exercise, drugs and cardiovascular education materials. The physician can communicate electronically with the infomediary site to obtain patient test results and formulate a patient treatment plan from the diet, exercise and drug data. The physician can electronically communicate treatment plans to the patient through a record in the infomediary site. The patient can electronically communicate compliance information to the physician through the patient record. The infomediary site may also provide a case manager to provide initial draft treatment plans to the physician, gather patient history data and/or patient treatment plan compliance data.

8 Claims, 25 Drawing Sheets

U.S. PATENT DOCUMENTS

| | | | | |
|---|---|---|---|---|
| 5,925,229 | A * | 7/1999 | Krauss et al. | 204/606 |
| 5,935,060 | A | 8/1999 | Iliff | 600/300 |
| 5,950,632 | A | 9/1999 | Reber | 128/898 |
| 5,956,689 | A | 9/1999 | Everhart | 705/3 |
| 5,960,403 | A * | 9/1999 | Brown | 705/2 |
| 5,964,700 | A | 10/1999 | Tallman et al. | 600/300 |
| 5,967,975 | A | 10/1999 | Ridgeway | 600/300 |
| 5,974,124 | A | 10/1999 | Schlueter, Jr. | 379/106.02 |
| 5,991,729 | A | 11/1999 | Barry et al. | 705/3 |
| 5,993,001 | A | 11/1999 | Bursell | 351/212 |
| 6,006,191 | A | 12/1999 | DiRienzo | 705/2 |
| 6,007,459 | A | 12/1999 | Burgess | 482/4 |
| 6,018,713 | A | 1/2000 | Coli et al. | 705/2 |
| 6,022,315 | A | 2/2000 | Iliff | 600/300 |
| 6,024,699 | A * | 2/2000 | Surwit et al. | 600/300 |
| 6,027,217 | A | 2/2000 | McClure | 351/224 |
| 6,038,469 | A | 3/2000 | Karlsson et al. | 600/512 |
| 6,047,259 | A | 4/2000 | Campbell | 705/3 |
| 6,063,026 | A | 5/2000 | Schauss | 600/300 |
| 6,063,043 | A | 5/2000 | Meyer | 600/586 |
| 6,206,829 | B1 * | 3/2001 | Iliff | 600/300 |
| 6,234,964 | B1 * | 5/2001 | Iliff | 600/300 |
| 6,246,992 | B1 * | 6/2001 | Brown | 705/2 |
| 6,454,705 | B1 * | 9/2002 | Cosentino et al. | 600/300 |
| 6,454,709 | B1 * | 9/2002 | Kleinschmidt et al. | 600/300 |
| 6,468,210 | B1 * | 10/2002 | Iliff | 600/300 |
| 6,470,320 | B1 * | 10/2002 | Hildebrand et al. | 705/3 |
| 6,484,144 | B2 * | 11/2002 | Martin et al. | 705/2 |
| 6,576,471 | B2 * | 6/2003 | Otvos | 436/71 |
| 6,602,469 | B1 | 8/2003 | Maus et al. | |
| 2002/0087276 | A1 * | 7/2002 | Otvos | 702/24 |
| 2003/0119194 | A1 * | 6/2003 | Otvos | 436/71 |
| 2003/0208108 | A1 | 11/2003 | Shewmake | |

OTHER PUBLICATIONS

Sublett, John W., et al, "Design and implementation of a Digital teleultrasound System for Real-Time Remote Diagnosis," University of Virginia.

Orphanoudakis, Stelios C., "Integrated Telemedicine Networks and Added-Value Services," Jun. 1998.

NASA Ames Research Center: *the Virtual Collaborative Clinic: An Experiment In Telemedicine Technology*.

Rubin, D.N., et al, "Telemedicine In Cardiology," American College of Cardiology.

Short, B.C., et al "Quality Assessment and Lipid Management: Considerations for Computer Databases for tracking Patients," Baylor College of Medicine.

Flower, J., et al. "Technological Advances and the Next 50 Years of Cardiology," American College of Cardiology.

Popine, C.J., et al., "Rationale and Design of the International Verapamil Sr/Trandolapril Study (INVEST): An Internet-based Randomized Trial in Coronary Artetry Disease Patients with Hypertension," The American College of Cardiology.

Klocke, F.J., et al "Role of the American College of Cardiology in Promoting and Maintaining the Delivery of Quality Cardiovascular Care in the Future," The American College of Cardiology.

American Telemedicine Association; www.atmeda.org.

Fletcher Allen Health Care's Telemedicine Program; www.vtmednet.org/telemedicine.

Department of Defense Telemedicine Site; www.matmo.org.

PictureTel Corporation; www.pictel.com.

Telemedicine Information Exchange; www.telemed.org.

Telehealth Networks Magazine; www.dis.port.ac.uk/ndtm/>.

Telemedlaw; www.legamed.com.

NASA Telemedicine; www.hq.nasa.gov/office/olmsa/aeromed/telemed>.

Commercial On-Line Databases (See Appendix A Attached).

Taddei, A., et al; "Medical Record System for Cardiology and Cardiac Surgery"; Computers in Cardiology, 1999; 26:85-88.

Pira, S., et al, "Supporting Asynchronous Telemedicine: Multimedia Mail vs. The World Wide Web vs. Replicated Databases"; IEEE Transaction on Information Technology in Biomedicine; 1988; 341-344.

Bai, J., et al; "Design and Development of an Interactive Medical Teleconsultation System over the World Wide Web"; IEE Transactions on Information Technology in Boimedicine, vol. 2, No. 2, Jun. 1998.

\* cited by examiner

4myheart.com
personalized cardiovascular wellness management

Physicians Front Desk | About 4myheart.com | Contact

Welcome to the Physician's Front Desk
Wednesday, Ma

WELCOME
- 161 — Patient Activity
- 162 — Patient List
- 163 — E-Mail
- 164 — My Statistics
- 165 — End of Day Report
- 166 — Preferences
- 167 — Reference
- 168 — News
- 169 — Product Review

My Statistics — 174

| Patients | Pattern B | L(s) | Complying to Excercise | Complying t |
|---|---|---|---|---|
| Myself | 20% | 20% | 20% | 20% |
| Community | 20% | 20% | 20% | 20% |

Patient Activity — 176

| Patients | Email | New Test | FAQ | Complian |
|---|---|---|---|---|
| 5 | 20 | 3 | 6 | 4 |

Professional News — 178

Current Major Headlines
Current major headline introduction
Major Headline Topic 1
Major Headline Topic 2

Current News
- News Headline
- News Headline
- News Headline
- News Headline
- News Headline

Upcoming Events

| | |
|---|---|
| 2/12/2000 to 2/12/2010 | Event Title / Event Location |
| 2/13/2000 to 2/17/2010 | Event Title / Event Location |
| 2/13/2000 to 2/17/2010 | Event Title / Event Location |

![4myheart.com screenshot showing Patient Folder with Diet Prescription]

Patient Joeseph R.[?]
Gender Male
Age 57
Birth Date 4-16-43
ID Number T25048

Salient Medical History
Information

Current Medications
Information

Diet Prescription

Total Daily Calories

Select Daily Caloric Amount 2000 3000 4000

Total Caloric Breakdown

| | | | |
|---|---|---|---|
| 6% | Saturated Fat | 10% | Complex Carbohydrates |
| 15% | Polyunsaturated Fat | 45% | Simple Carbohydrates |
| 10% | Monounsaturated Fat | 15% | Protiens |
| 6% | Saturated Fat | 10% | Complex Carbohydrates |
| 15% | Polyunsaturated Fat | 45% | Simple Carbohydrates |
| 10% | Monounsaturated Fat | 15% | Protiens |
| 6% | Saturated Fat | 10% | Complex Carbohydrates |
| 15% | Polyunsaturated Fat | 45% | Simple Carbohydrates |
| 10% | Monounsaturated Fat | 15% | Protiens |
| 6% | Saturated Fat | 10% | Complex Carbohydrates |
| 15% | Polyunsaturated Fat | 45% | Simple Carbohydrates |
| 10% | Monounsaturated Fat | 15% | Protiens |

Notes

Figure 12

4myheart.com
*personalized cardiovascular wellness management*

Patient Reception Area    About 4myheart.com    Contact U

Welcome to the Patient's Reception Area

WELCOME

- Test Results — 351
- Compliance/Visit — 352
- E-Mail — 353
- Products — 354
- Preferences — 355
- 356
- Reference — 357
- News — 358
- Physician Profile — 359

Patient: D*****, Frank
Gender: M
Age: 71
Birth Date: 10-20-1927
ID Number: T14523

Wednesday, Mar

Test Results — 341

| date | tests taken | comments | view |
|---|---|---|---|
| 5-28-1999 | HDL GGE | Comments from cardiologist | |
| 5-28-1999 | LDL GGE | Comments from cardiologist | |
| 5-28-1999 | LIPID PANEL | Comments from cardiologist | |

Diagnosis — 342

| Date | Diagnosis |
|---|---|
| Date | Diagnosis 1 |
| Date | Diagnosis 2 |
| Date | Diagnosis 3 |

Treatment Plan — 343

Overview
This will be a brief paragraph explaining the comments of the treatment plan below.

Email Inbox — 344

| date | time | subject | status | did |
|---|---|---|---|---|
| 1/22/2000 | 12:36pm | How are you feeling today? | | |
| 1/22/2000 | 1:14pm | About your breathing trouble... | | |

MEDICINE TRACKER

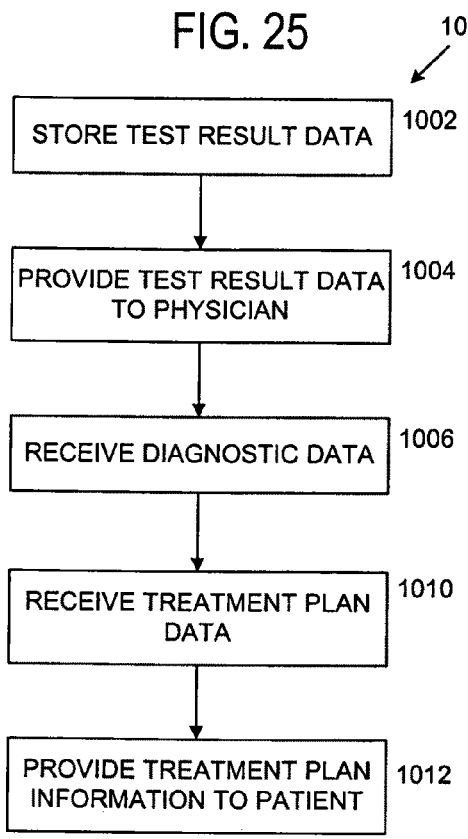
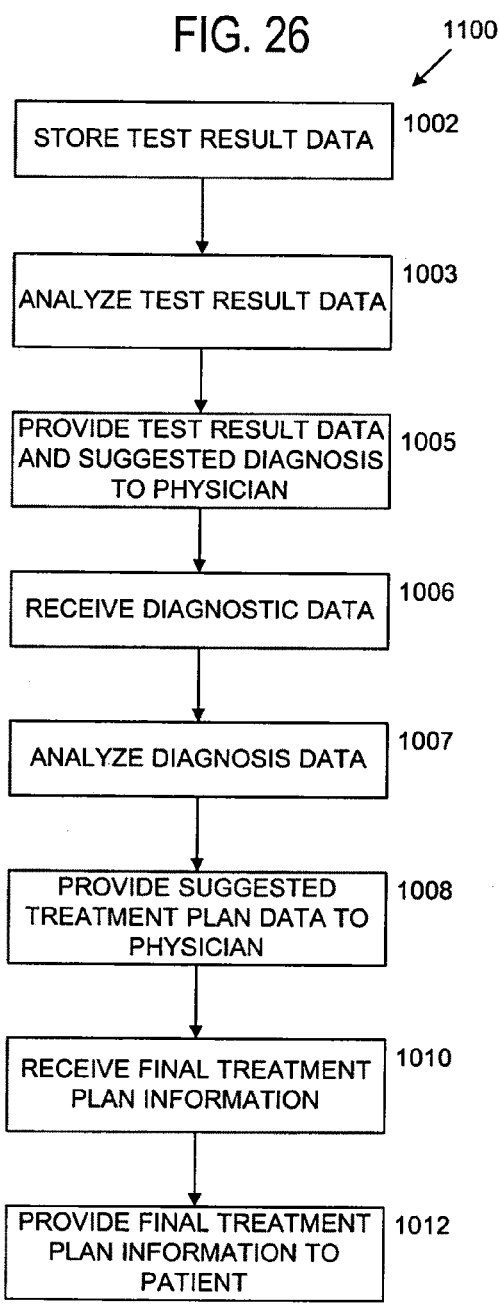

CARDIOVASCULAR HEALTHCARE MANAGEMENT SYSTEM AND METHOD

This application claims the benefit under 35 U.S.C. § 119(e) of U.S. Provisional Patent Application Ser. No. 60/126,003, filed Mar. 24, 1999, entitled "Method for Individualized Patient Treatment" for all common subject matter disclosed therein, and the contents of said application are hereby incorporated by reference. This application also claims the benefit under 35 U.S.C. § 119(e) of U.S. Provisional Patent Application Ser. No. 60/168,354, filed Dec. 1, 1999, entitled "Method for Individualized Patient Treatment" for all common subject matter disclosed therein, and the contents of said application are hereby incorporated by reference.

BACKGROUND OF THE INVENTION

1. Field of the Invention

This invention is in the field of managing patient health through an automated online database. More particularly, the system provides for diagnosis and management of cardiovascular disease and includes assessment of cardiovascular risk factors and providing patient treatment plans.

2. Background of the Art

The art describes cardiovascular risk factors such as age, smoking, weight, family history, blood pressure, lipid profiles including low density lipoprotein (LDL) and high density lipoprotein (HDL) and subclasses (fractions) of LDL and HDL. Methods for measuring these factors and relating them to patient treatment are also known. Generally, physicians assess a patient's risk factors, make a diagnosis based on test results and symptoms and manage patient treatment through drugs, exercise, diet and a variety of surgical techniques. Instructions are generally given directly to the patient by the physician. Patient compliance generally involves interview in follow-up office visits.

SUMMARY OF THE INVENTION

The present invention provides a cardiovascular healthcare management system that has an infomediary site, which includes databases with cardiovascular disease risk assessment and cardiovascular disease management information. Patient data is stored in an information database, and patient test results are stored in a clinical database, both of which are selectively accessible to both physicians and patients. Patients' test results and personal information are thus added to the databases and may be viewed by the physician to assist in diagnosis.

A knowledge base may also be included to provide further diagnostic data to a physician. The knowledge base may be used as part of a diagnostic engine that analyzes test results to determine whether they meet certain criteria indicative of a patient's health condition, or might simply contain descriptions of risk factors or combinations of risk factors that are believed to be indicative of specific health conditions. The knowledge base of the preferred embodiment includes software referred to herein as a diagnostic engine that performs risk assessments on specific test results and stores risk assessment information in the database for later viewing by the physician to further assist in diagnosis.

The database also has information related to managing the patient's cardiovascular health. The cardiovascular disease (CVD) management system provides for the physician having electronic access to the infomediary site for receiving patient test results and entering diagnosis and treatment information to facilitate the building of a treatment plan. The treatment plan is created after viewing test results and relevant patient data and entering any supplemental information including a diagnosis. The treatment plan may include a recommended diet, prescription (and nonprescription) drugs, an exercise regimen, and alternate cardiovascular products that may be available for purchase through the infomediary site (e.g., blood pressure cuffs to monitor blood pressure, anti-embolism support hosiery, dietary products, educational materials, etc.). Portions of the treatment plan are preferably derived from templates that are provided by the infomediary site 100. In addition, the infomediary site may present templates having the most relevant treatment plan components based in part upon the physician's previously entered diagnosis information.

The system also provides for electronic communication between the patient and physician by way of access to one or more records in the infomediary site. In this way, a physician can electronically provide cardiovascular disease management instruction such as diet, exercise and medication to the patient and the patient can electronically provide compliance information to the physician directly or indirectly via an alternate input device.

In another aspect of the infomediary site, a case manager may be provided to collect and input initial patient data and to perform follow-up services like collecting and inputting compliance data to the infomediary site. The case manager may also review initial patient history, test results, and then create a suggested treatment plan for the cardiologist to review. The cardiologist may accept the treatment plan unchanged or modify it, and then electronically release the treatment plan to the patient's folder, which stores personalized information within the CVD management system site. The case manager also proactively contacts patients to advise and assist in the implementation of their treatment plan.

Alternatively, tele-medicine devices may be used to gather compliance information for submission to the infomediary site.

BRIEF DESCRIPTION OF THE FIGURES

FIG. 3 is the physician's welcome screen;
FIGS. 4-12 show additional screens available to the physicians;
FIG. 13 is the patient's welcome screen;
FIGS. 14-17 show additional screens available to the patient;
FIGS. 25 and 26 are flow diagrams for methods associated with the infomediary site.

DETAILED DESCRIPTION OF THE INVENTION

Figure 1:
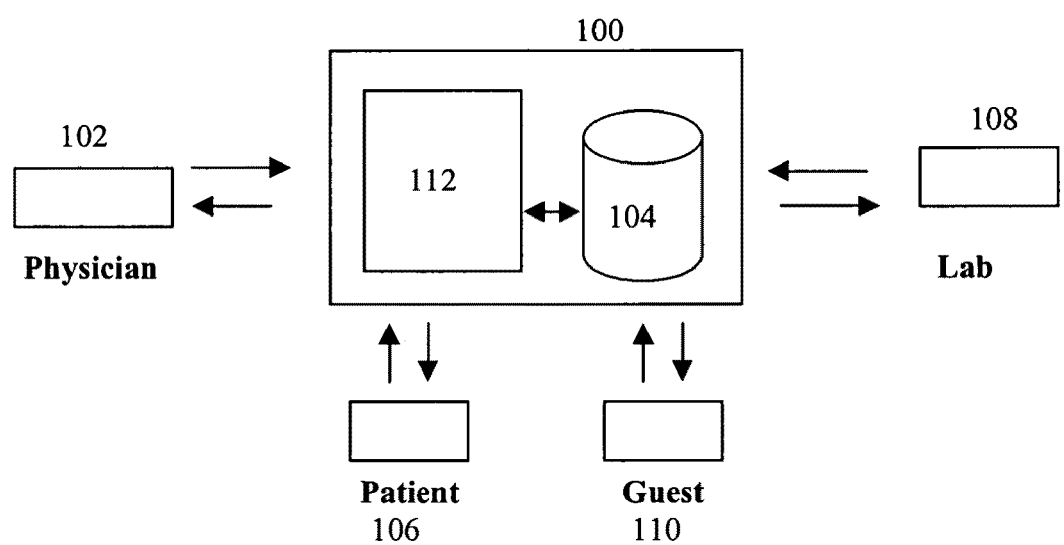
FIG. 1 is a block diagram of the infomediary site.

FIG. 1 illustrates a schematic of the infomediary site 100. It shows physician 102 in communication with the site 100 to retrieve test results from a database 104, communication of diagnosis information and a treatment plan or other data to the database 104 by way of server 112. The server scripts 112 generally provide a "front end" to access the records within database 104. Specified records of database 104 are also made accessible to the respective patients 106. The patient 106 can view test results, treatment plans, and communications from the physician 102, and communicate compliance information to the physician 102. The lab 108 provides for inputting test results into the site. There may also be an optional guest 110 access for reviewing limited data in the system.

Physician Access

The physicians 102 can log-on to the infomediary site 100 and communicate with patients 106 and the infomediary site 100 to manage the patient's cardiovascular healthcare. The physician 102 first logs in to the site 100 at the login screen 150 by entering a username in field 152, a password 154, and submitting the data by clicking on submit button 156. The physician is then presented with the welcome screen 160 as shown in FIG. 3. The interface made up of the web pages that provide physician access to the site is referred to herein as the physician data access interface. The physician welcome screen 160 includes a navigation bar having a plurality of links represented by buttons 161-169. The physician welcome screen also includes summary views of certain data such as the physician's statistics at tab 174, patient activity at tab 176 and professional news at tab 178. Tabs 174, 176, and 178 are also links to more detailed screens, which can also be accessed by buttons 164, 161, and 168, respectively. Preferably, the physician is able to customize his or her own welcome screen to provide customized summary information.

Figure 4:
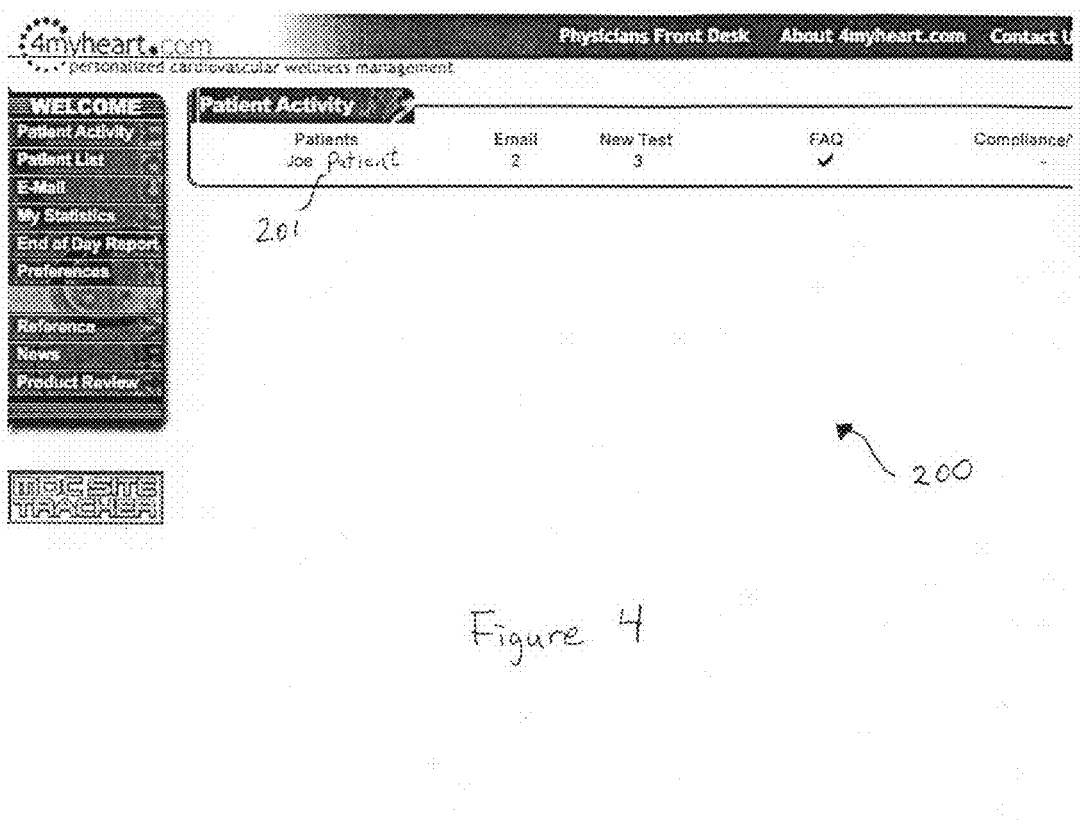
Figure 5:
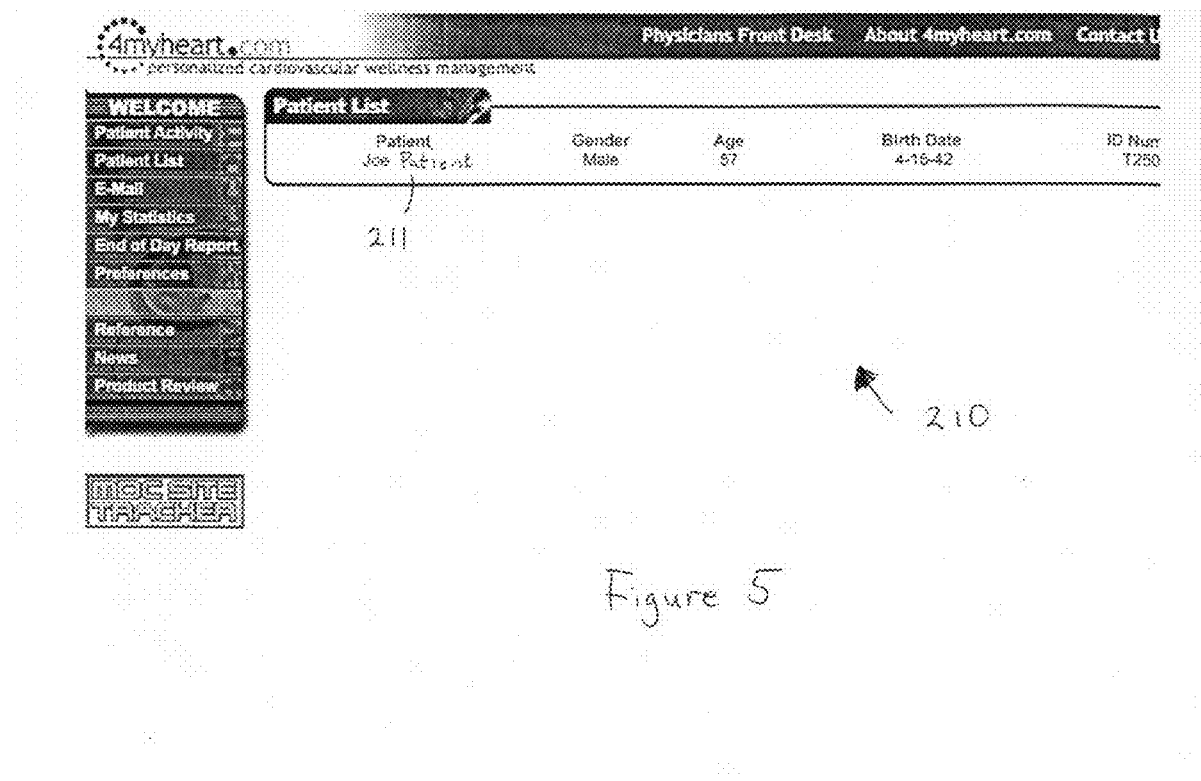

The link underlying patient activity button 161 brings the physician to the patient activity screen 200 as shown in FIG. 4. The patient activity screen 200 is generated by ASP script physician_patient_activity.asp. The patient activity screen 200 provides a list of patients who may need attention. The physician's attention may be needed due to the receipt of new test results (input by the Lab 108), the receipt of patient correspondence or compliance data, or the like. The link underlying patient list button 162 brings the physician to the patient list screen 210 as shown in FIG. 5, which is preferably generated by the ASP script physician_patient_list.asp. The screen 210 contains a list of all current (and/or past) patients for that particular physician. The link underlying e-mail button 163 brings the physician to the email screen 220 as shown in FIG. 6, which is preferably generated by ASP script physician_email_detail.asp.

Figure 6:
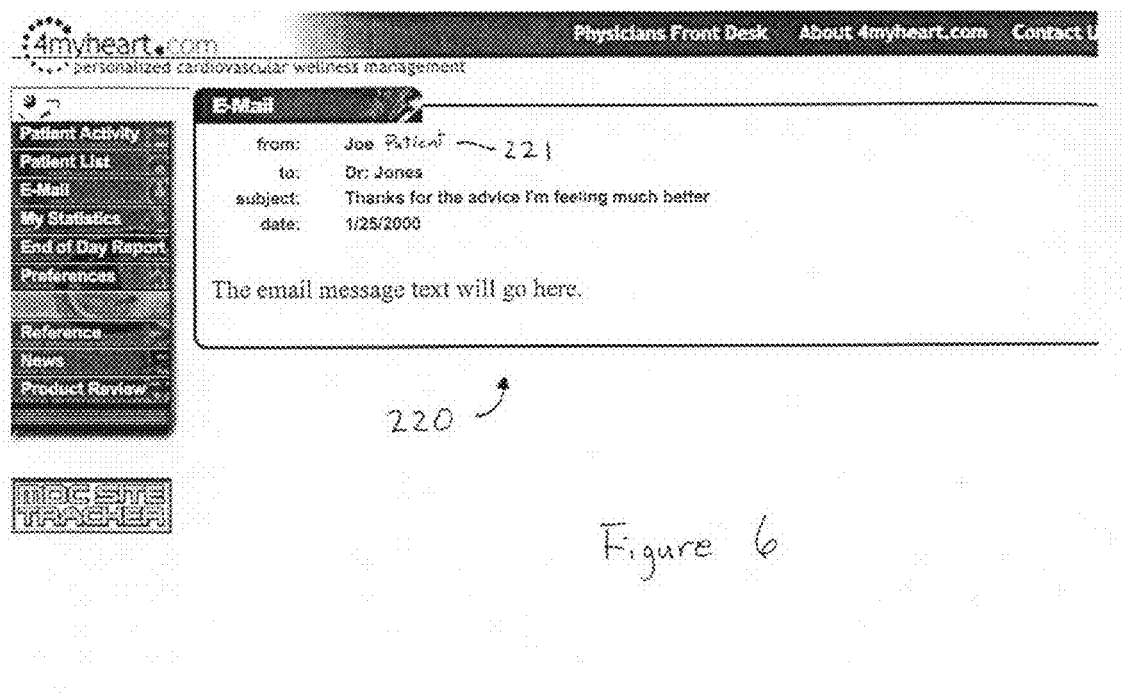
Figure 7:
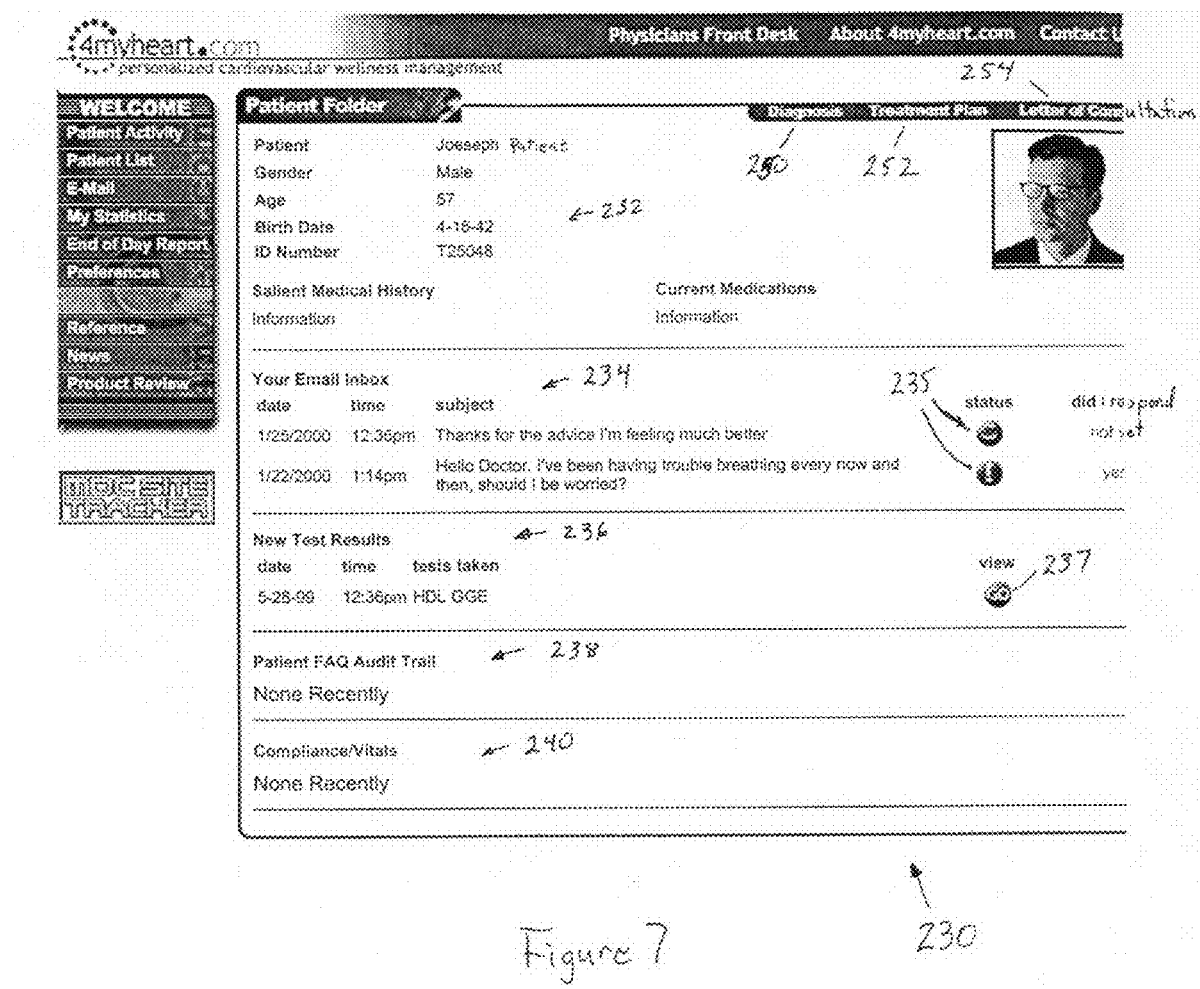

The names of one or more of the patients of the particular physician are displayed on the screens in FIGS. 4-6. Preferably, the patient name (e.g., 201, 211, and 221) is also a hypertext link to the patient's data file, thereby providing the physician with convenient access to the detailed patient record displayed on a patient folder screen, one of which is shown at 230 in FIG. 7. The patient folder 230 is preferably generated by ASP script physician_patient activity_details.asp.

The patient folder 230 has a general patient information display area 232, patient correspondence display area 234, test results display area 236, FAQ audit trail display area 238, and compliance data display area 240. The patient folder may also contain patient billing and insurance coverage and/or insurance carrier information (not shown). The physician can create initial patient histories by utilizing and editing standard forms. Alternatively, a patient may provide medical background information to the infomediary site 100, either by way of the network through an initial registration procedure, or by calling a data entry specialist provided by the infomediary site 100. Preferably, the infomediary site provides the physician with the services of the case manager, who is typically a lipid nurse, nurse, physician assistant, or other qualified person. The case manager may also act as the data entry specialist.

The general patient information display area 232 contains general patient information including name, birth date, medications, insurance information, and salient medical history information, etc.

The patient correspondence display area 234 is referred to herein as a communication interface. It is presented as an email inbox, but preferably does not operate as standard internet email. That is, physicians preferably communicate with their patients by way of the database 104 located at the infomediary site 100. Referring back to FIG. 1, the physicians preferably enter data to be communicated into one or more records of database 104 by way of the infomediary server scripts 112. The server scripts 112 process physician and patient "email" entries to the database 104 and provide an email-type interface. Preferably, actual emails are not sent by the physician, patient or infomediary site 100. Standard email may be utilized in an alternative embodiment; however, less monitoring and control (e.g., delivery verification) of the communication is available when standard email is used. To generate an internet email from an ASP script, for example, an ASP server running with the Windows NT® 4.0 Operating System Option Pack installed and Microsoft®SMTP Service (from the Option Pack) running may use the CDONTS component. The correspondence display area 234 also shows the status of the email with icons 235, as well as an indication of whether the physician has replied to the patient's email. Of course, the infomediary site may utilize standard internet email to notify the patient of upcoming appointments for lab test work, doctor office visits, compliance conferences with case managers, or to request that the patient log in to the infomediary site to view newly posted treatment plans, compliance requests, or for other similar notifications.

The FAQ audit trail display area 238 allows the physician to view which general information the particular patient has accessed over the network. This may reveal additional information to the physician about the patient's concerns that the patient would not otherwise convey to his physician. The compliance data display area 240 provides the physician with information provided by the patient as to whether the patient has been complying with his or her treatment plan. Preferably, the patient provides information to the case manager who, in accordance with the treatment plan, initiates follow-up contact with the patient. The case manager solicits information regarding the patient's compliance with the treatment plan such as diet, exercise, medication, and weight and blood pressure, if available. The case manager may input the compliance data into the information database 104. Alternatively, the patient may input the data directly via the infomediary site 100. In addition, with reference to FIG. 24, the patient may utilize tele-medicine devices to provide compliance-type data. For example, health related measurement devices such as a weight scale 115, blood pressure cuff 116, electrocardiogram devices 117, and the like, may be connected to the network 101 for transmitting data to the infomediary site 100. The device may be connected directly to the network 101, or via the patient's home computer, or through a networking device in the patient's home. The tele-medicine devices may also be made available at another location such as a drug store, etc. The device preferably communicates the measured data and automatically submits the data or compliance information to the infomediary site. The tele-medicine device may include software (i.e., a resident device driver, or java-type plug in module) to format appropriately the identification and authentication information along with the data for transmission to the site 100. The physician may be notified of the presence of compliance data either via the email inbox 234 or by listing that patient in the patient activity display screen 200.

Figure 8:
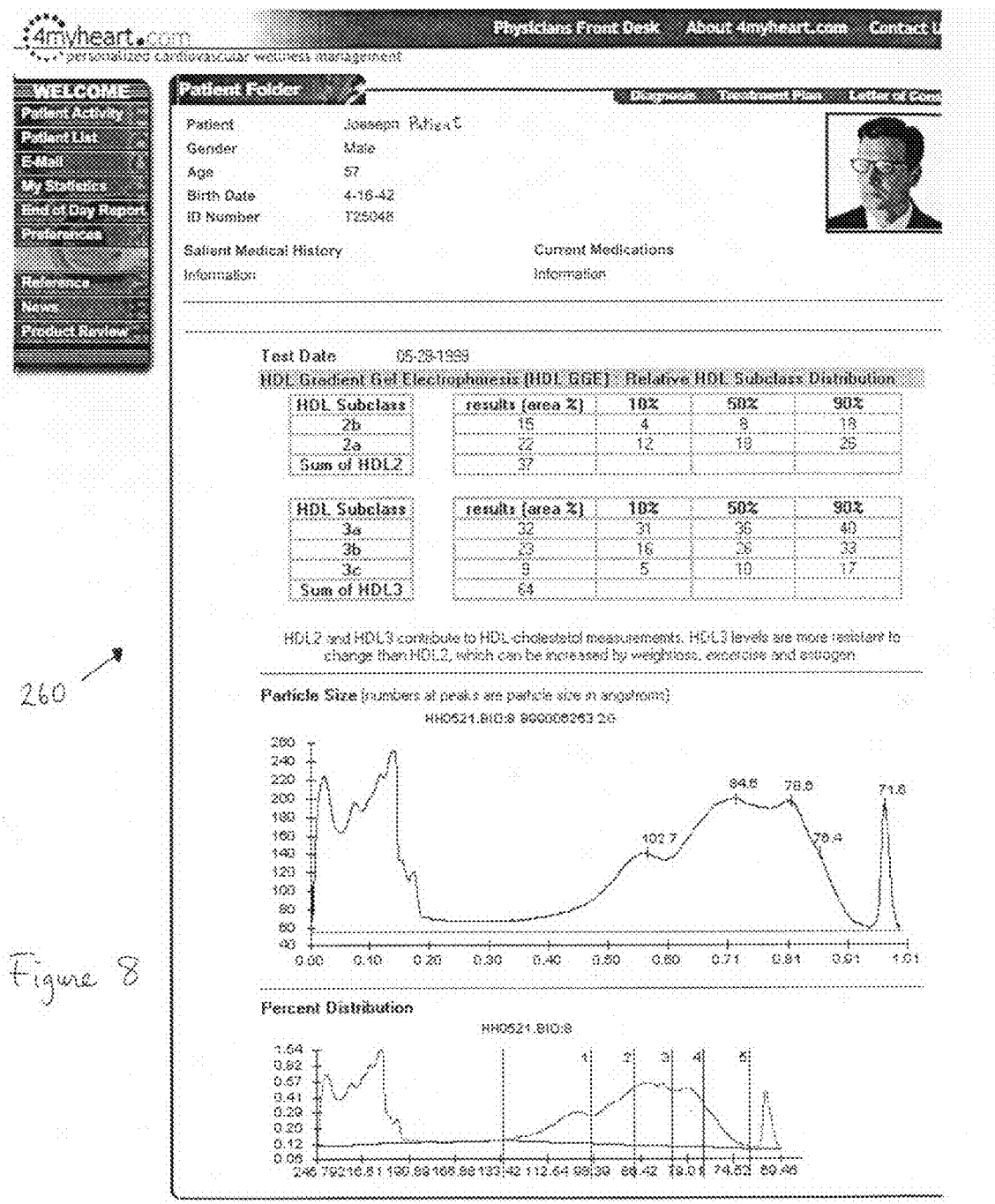

The test results display area 236 shows recent test work, and a test results link 237 to allow the physician to view the test results. A typical test results screen 260 is shown in FIG. 8. In particular, the test results of FIG. 8 show the patient's HDL Gradient Gel Electrophoresis in tabular form by HDL subclass, and in graphical form. As seen in the table, the test results show the normalized percentages of HDL subfractions, as well some points (10%, 50% and 90%) on the distribution of normalized percentages. Specifically, the table shows that 10% of people in the sample have a normalized percentage of HDL Subclass 2b of 4% or more, while 90% have a normalized percentage of 18% or less, with the 50% point being 8%. Thus, for example, the physician can see that the particular 2b Subclass test result of 15% is generally within the higher ranges. It should be noted that more complete tables may be provided to show finer resolution of percentages. It should also be noted that the people in the sample to which the test results are compared may vary. In particular, it is often helpful for a physician to be able to compare test results to a population having a similar diagnosis. To illustrate this, in the example shown in FIG. 8, the percentages listed are for those people diagnosed with coronary artery disease (CAD). Thus, the physician is able to determine that the particular results show levels of HDL Subclass 2a and 2b that are higher than average compared to people with CAD, and levels of HDL Subclass 3a, 3b and 3c that are lower than average compared to that same population, and interpret the results accordingly. In a preferred embodiment the physician may dynamically select the reference population to further assist in making a diagnosis. The doctor preferably has the ability to adjust a number of analysis parameters to customize the test result analysis or comparison. The parameters may specify aspects of the general population used as a reference and may include age range, diagnoses, symptoms, LDL and HDL subfraction ranges, etc. The site preferably provides default ranges of many analysis parameters to yield comparisons that have been determined (via research, data mining, etc.) to be useful in the diagnosis or treatment of CVD.

The physician can also view and print current and prior test results including patient personal information—name, address and telephone number. With the infomediary site 100 the physician can view cardiovascular risks from the knowledge base, including graphic representation of the patient's condition and test results. Charts or histograms comparing current and prior test results are also available from the infomediary site database.

Figure 9:
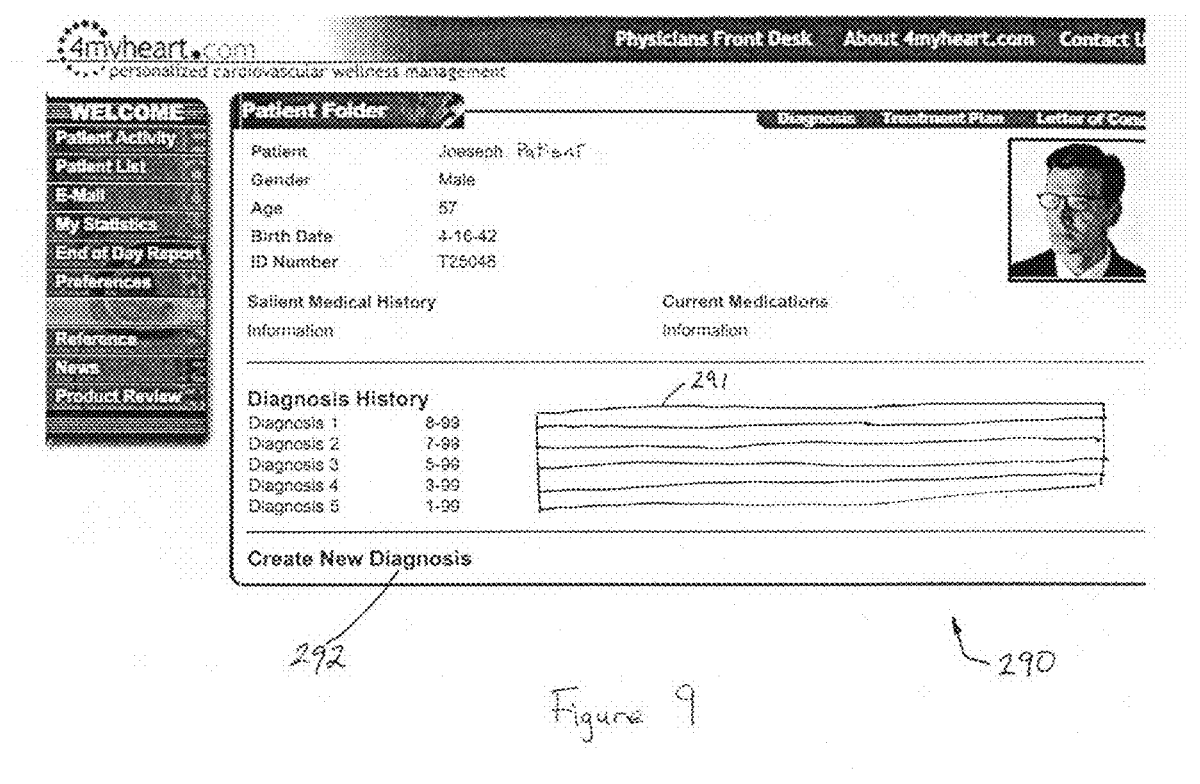

The patient folder 230 also includes a diagnosis link 250, treatment plan link 252 and letter of consultation link 254. The diagnosis link 250 retrieves the diagnosis screen 290 as shown in FIG. 9. The various diagnoses are shown, with the dates and summary information. For example, Diagnosis 1, made in 8/99, would be displayed in field 291. The physician may also create a new diagnosis using link 292.

Figure 10:
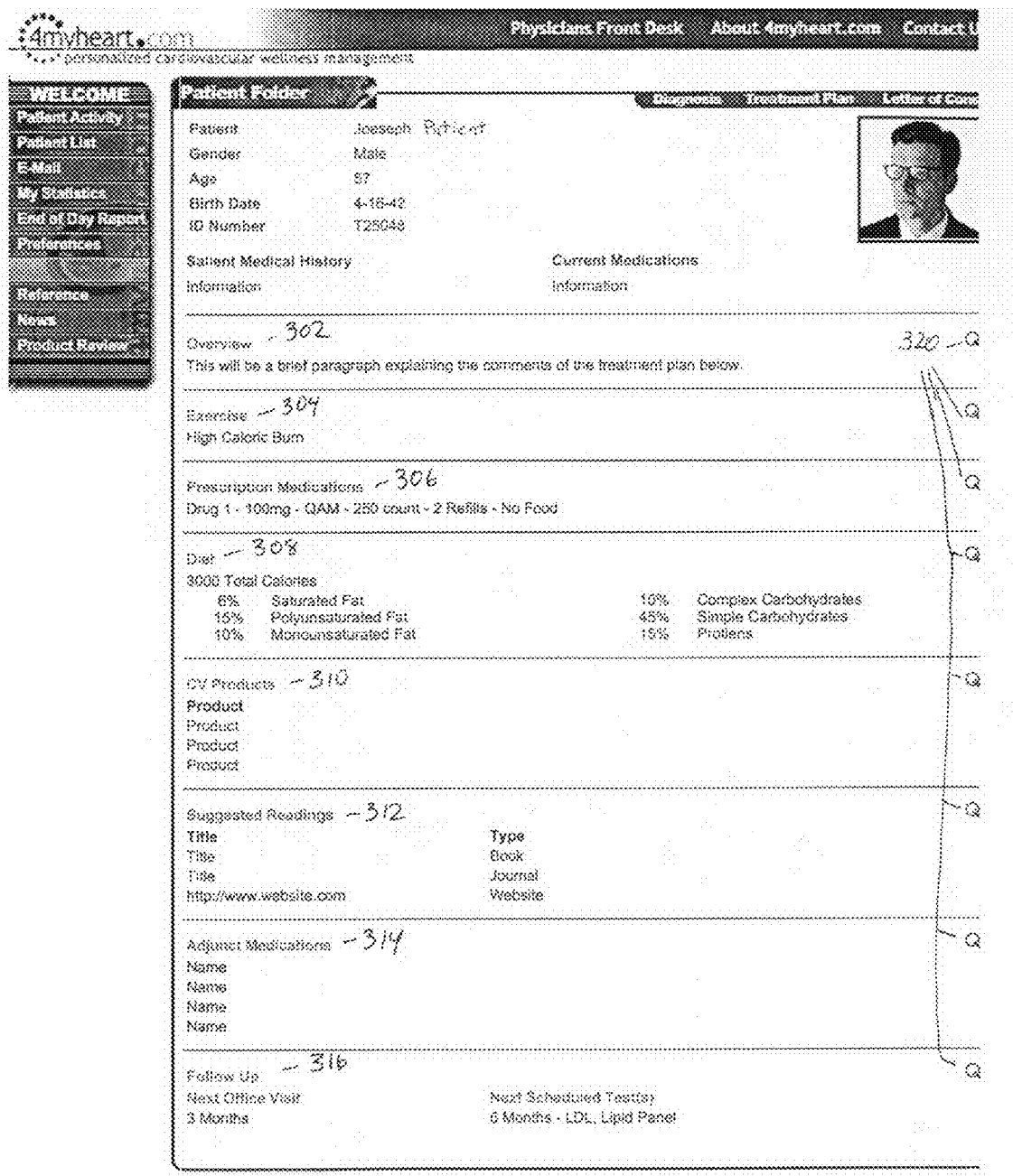
Figure 11:
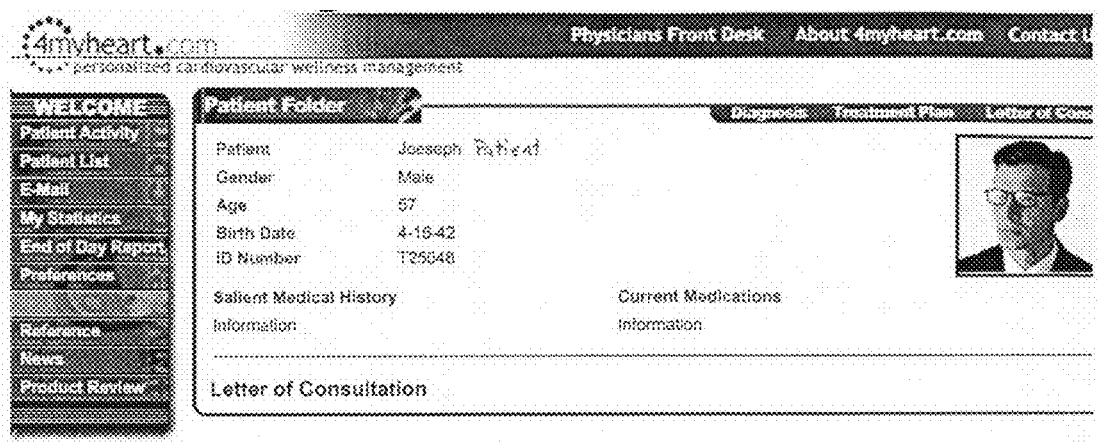

The treatment plan link 252 retrieves treatment plan screen 300 as shown in FIG. 10. The physician can create treatment plans for their patients from information in databases of the infomediary site 100. Treatment plan screen 320 includes overview display area 302 exercise display area 304, prescription medication display area 306 (generic and brand names, as well as the ability to print the prescription, or to specify a pharmacy to where the prescription may be electronically forwarded), diet display area 308, cardiovascular (CV) products display area 310, suggested readings display area 312 adjunct medications display area 314, and follow up display area 316. Each of the display areas 302-316 include links 320 to pages having further details relating to the respective sections. Preferably, the infomediary site provides the physician with a treatment plan template having the above-referenced components. The physician may select specific entries by a number of methods, including drop-down boxes, text boxes, bullet lists, etc. In addition, the template may initially provide selections that are consistent with the patient's data, including one or more of the following: test results, most recent test results, salient patient history, physician diagnosis data, etc. The finalized treatment plan may also be reviewed by the infomediary site to check for consistency of the plan with the same factors, and the physician's attention may be directed to aspects of the treatment plan that appear to conflict with the particular patient's data.

The link 254 to the letter of consultation allows the physician to construct letters of consultation from standard forms, patient data, standard paragraphs and phrases in the infomediary site database 104. These letters may be printed, stored and sent electronically or through regular mail.

The physician can also, through the infomediary site, visit e-commerce vendor's websites to purchase and recommend purchasing to their patients of prescription medication, adjunct medication, exercise equipment, dietary products, cardiovascular products and educational materials, such as reading materials, software, video recordings, etc.

The infomediary site 100 also provides physicians with educational materials such as recent news and suggested readings. The infomediary site 100 also provides physicians with administrative function capability. The physician can perform administrative functions, including creating or editing a physician profile, managing billing information and logs, and viewing daily activity summaries.

The infomediary site 100 may also perform insurance pre-certification to ensure that requested tests are covered by the patient's insurance. If the test is not covered, the physician and/or patient is notified, and further instructions are requested as to whether the physician and/or patient nevertheless wishes to have the test performed. The communication can be via telephone from the case manager, or via the infomediary site through the physician's "email" inbox. Typically, the infomediary will telephone the patient to inform them that the test is not covered or partially not covered. The nature of the test and the reason for the test is explained to the patient, and the patient may then elect to pay for the scheduled test or to decline the test. In the event the test is declined, the requesting physician is notified.

Patient Communication

Figure 2:
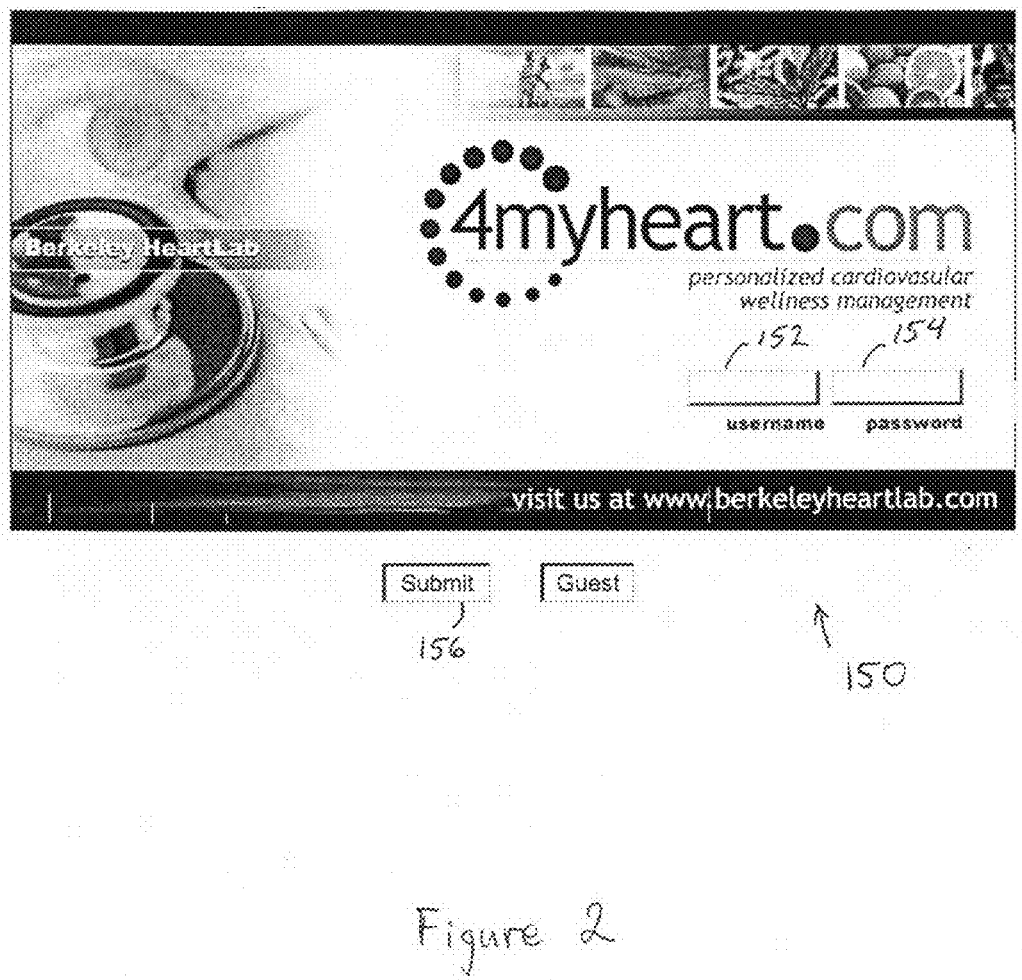
FIG. 2 is a login screen.
Figure 14:
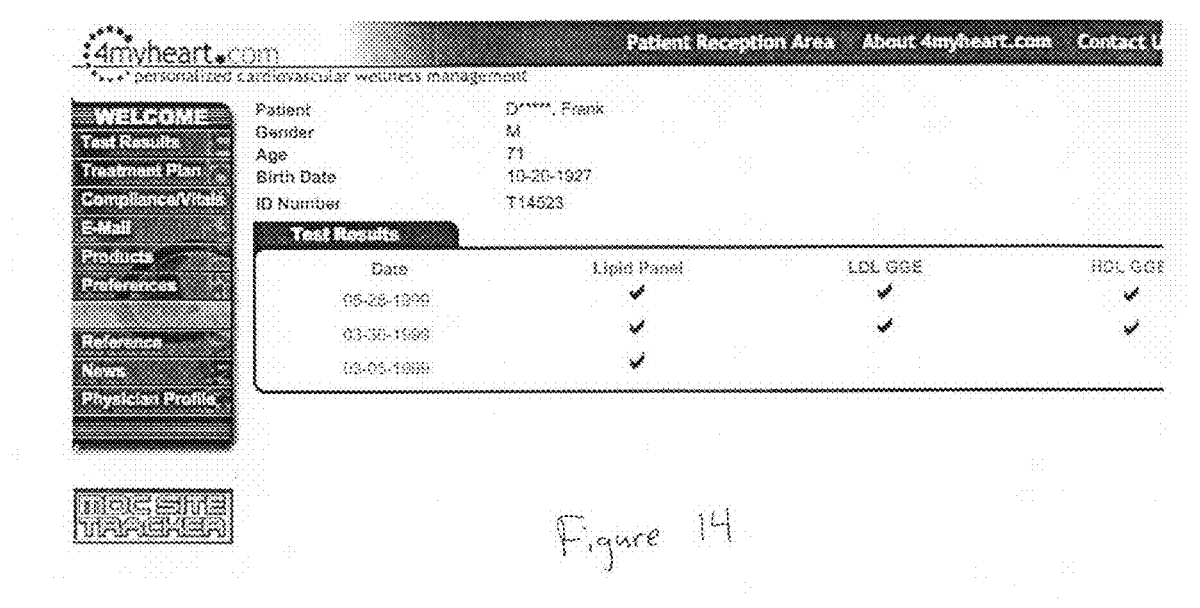
Figure 15:
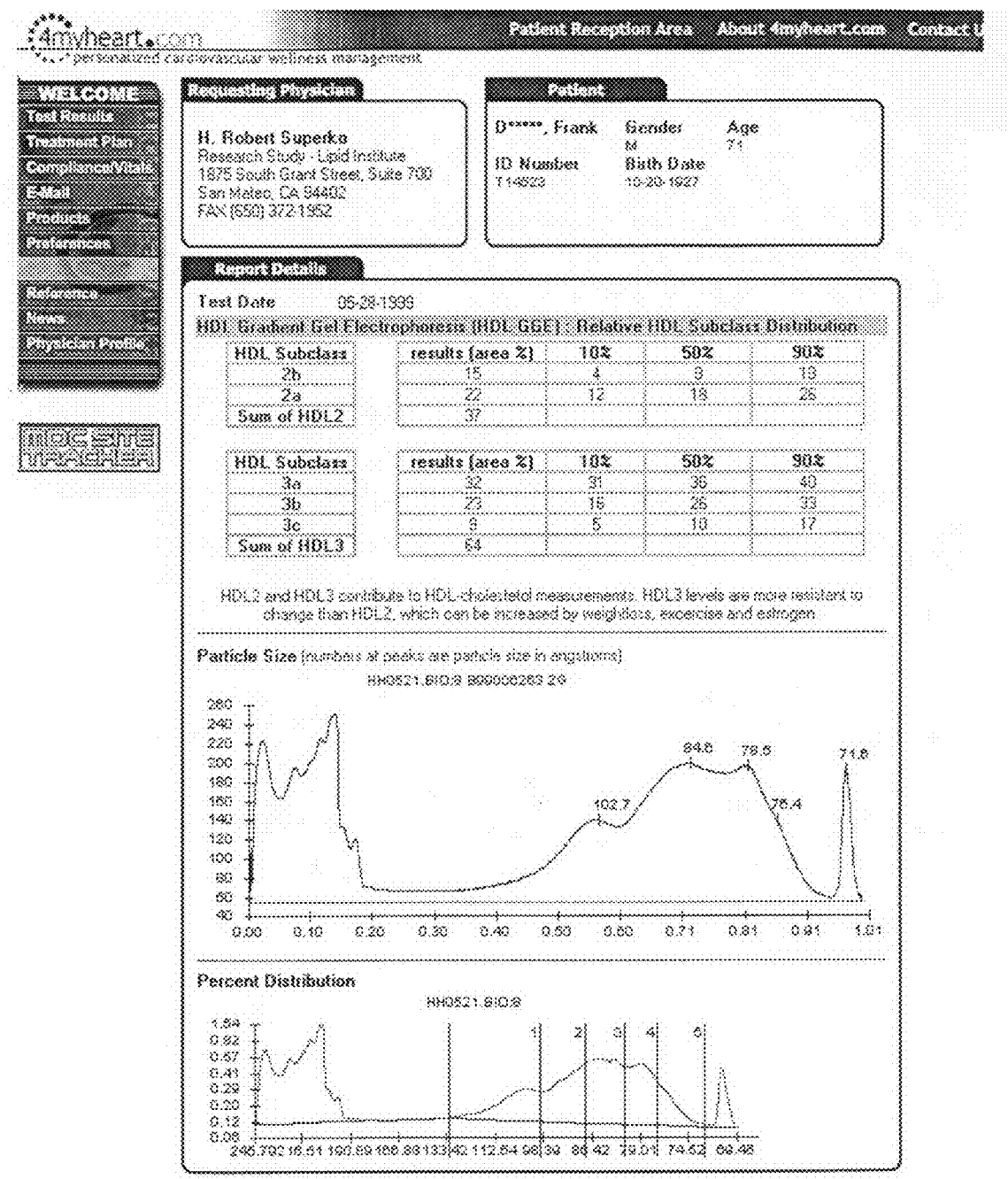
Figure 16:
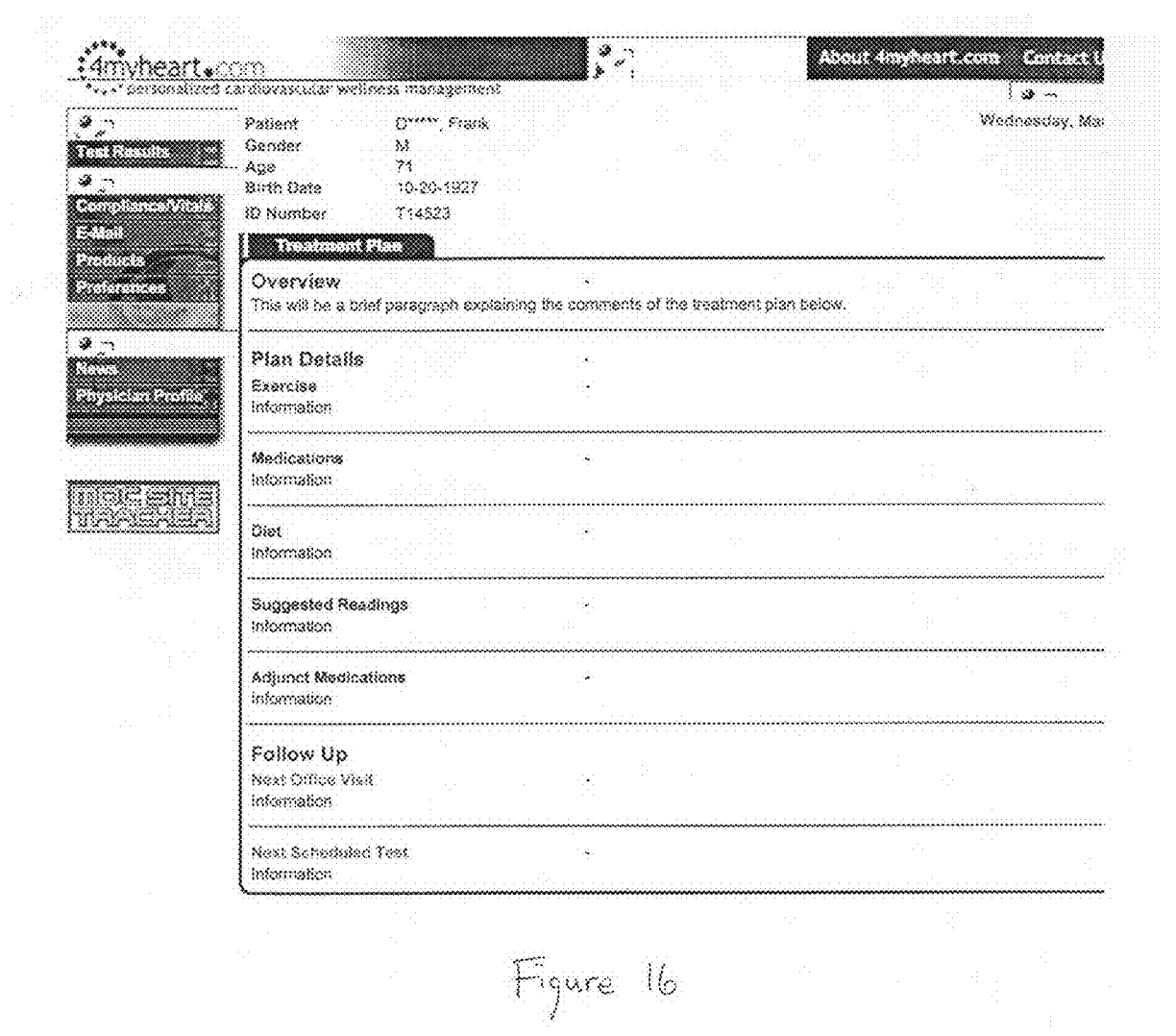
Figure 17:
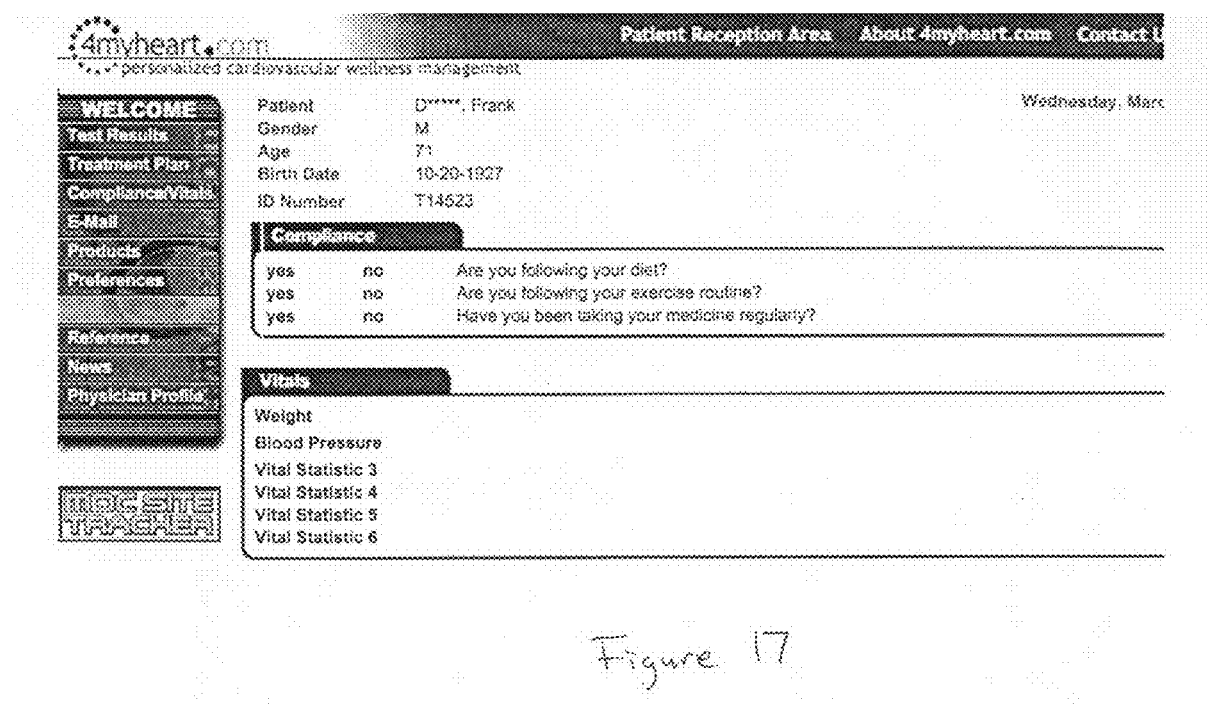

Patients can log-on to the infomediary site 100 and view screens that provide links to other pages or news. The patient 106 first logs in to the site 100 at the login screen 150 (FIG. 2) by entering a username in field 152, a password 154, and submitting the data by clicking on submit button 156. The patient is then presented with the patient welcome screen 340 as shown in FIG. 13. The patient welcome screen 340 includes a navigation bar having a plurality of links represented by buttons 351-359. The patient welcome screen also includes summary views of certain data such as test results 341 (as shown further in FIGS. 14 and 15), diagnosis information 342, treatment plans 343 (as shown further in FIG. 16), and email inbox 344. FIG. 17 depicts a compliance input screen that may be accessed directly by the patient, or by the case manager.

The patient can communicate with their physician through a communication interface. Preferably, this takes the form of mutual access to records in the infomediary site to obtain doctor treatment plans and report their compliance to the doctor as described above with respect to physician email. The patient can purchase products, including medications, adjunct medications, exercise equipment, dietary products, cardiovascular products and educational material directly from the infomediary site 100. Additionally, or alternatively, the infomediary site may contain links to vendor websites for purchasing the products from a third party.

Non-Doctor/Non-Patient Access to the Infomediary System

The infomediary system is adapted so that patient results from laboratory tests and related information can be inputted into the system. In particular, the site 100 may be accessed by the lab 108 so that test result data may be input directly through the web site server scripts. Alternatively, test result data may be input to the system by a data entry specialist or by a case manager.

The infomediary site may also be accessed by guests to the system. Guests may browse information, FAQ lists, physician profiles, physician referral services, or request further information or follow-up contact.

Cardiovascular Informatics

Figure 23:
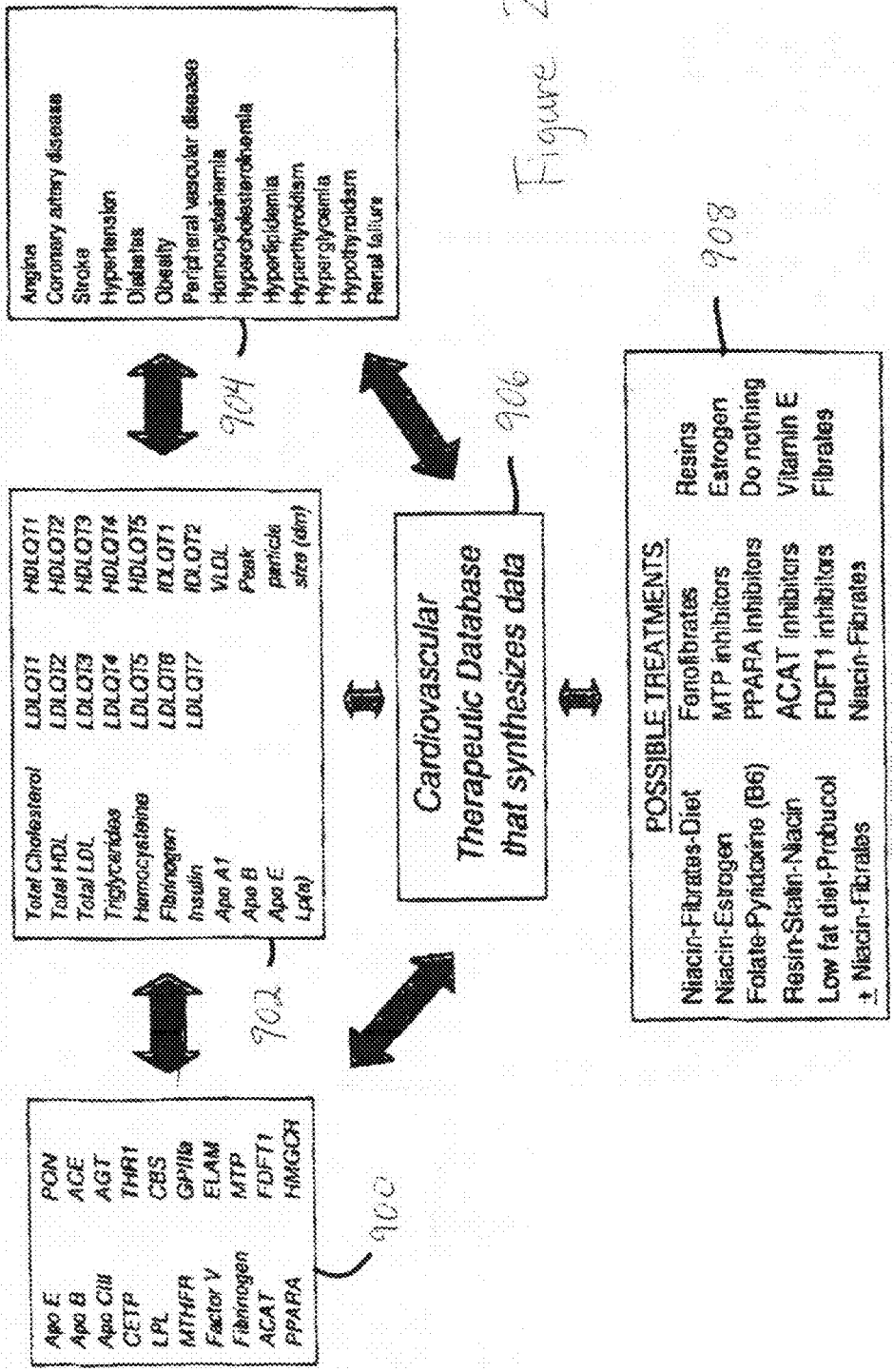
FIG. 23 is a schematic of the cardiovascular informatics.
Figure 24:
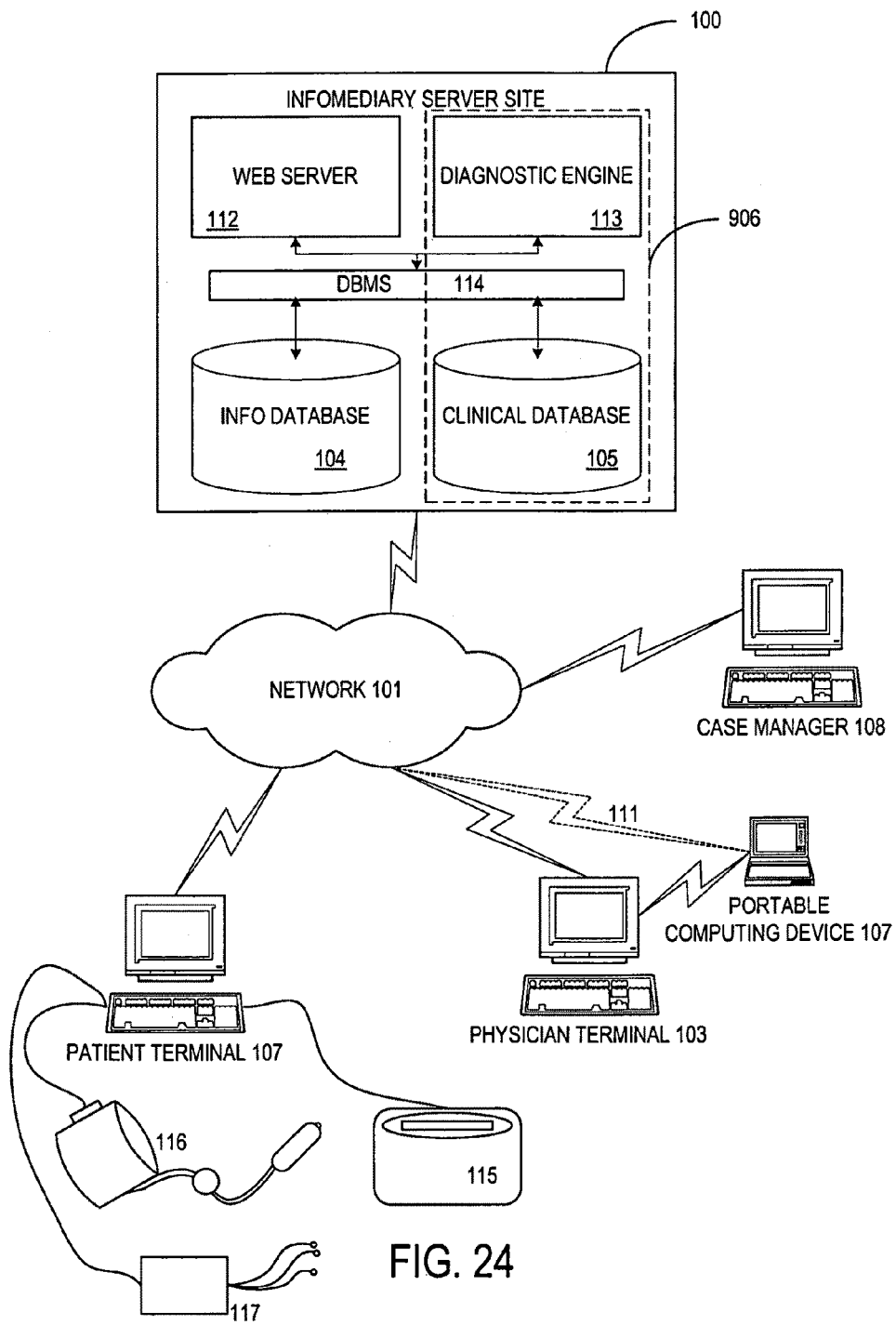
FIG. 24 is a more detailed block diagram of the infomediary site.

The infomediary site has advanced cardiovascular informatics related to factors such as genetics, diet, exercising and medication. The cardiovascular informatics is illustrated in FIGS. 23 and 24. Table 902 illustrates lipid-related data in the infomediary site 100. The relationship of lipids 902 to genetic markers 900 and other coronary risk and disease factors such as those listed in 904 are analyzed by and stored in the CV Therapeutic database 906. Of course, as an initial matter, an individual patient might not have every test listed in 900 and 902; however, the infomediary site includes a diagnostic engine 113 to identify whether any additional tests should be recommended to a physician. Note that tables 900, 902, 904 and 908 are shown in summary form, but generally take the form of relational database tables such as those shown in FIGS. 18-22, having ID fields, text fields, patient and test ID fields, etc.

Thus, a cardiovascular risk database is formed from the information in tables 900, 902, and 904 within clinical database 105. Each entry in tables 900 and 902 also includes fields to identify the patient ID, physician/client ID as necessary, and may optionally include one or more suggested diagnosis fields (not shown). The diagnosis fields may also be included in another table associated with the patient within clinical database 105 or information database 104. The diagnosis fields preferably contain diagnosis ID's corresponding to the diagnosis text shown in table 904. The diagnosis fields are populated by the diagnostic engine 113, and are used to convey the analytical results of the diagnostic engine to the physician through the physician access interface. The CV therapeutic database 906 includes algorithms to identify patterns of risk factors, and may compare inputted patient results for lipid subfractions to the normal values. The algorithms are shown in FIG. 24 as a diagnostic engine 113. These algorithms may take the form of software programs or scripts such as SQL scripts or the like. The diagnosis engine 113 preferably operates on new test results to identify those results (in combination with other risk factors) that fall within the parameters specified by the algorithm. Additionally, the CV therapeutic database 906 may analyze the lipid subfractions in combination with other patient data such as that listed in table 900 and 904. The results, including possible treatments 908, can then be related to the physician.

As described above, the measurement of the patient's lipids, genetic markers and disease and disorder risk factors and comparison to the database provides a patient's specific risk factors which can be related to possible treatments. Furthermore, the book "The Heart Disease Breakthrough" by Thomas Yannios, M.D. John Wiley & Sons in 1999 illustrates additional important principals in cardiovascular healthcare that are incorporated into the CV therapeutic database 906 and diagnostic engine 113. This book is incorporated herein by reference. The book points out the important role of LDL and HDL subfractions in cardiovascular disease. This book further discusses the role of genetics, diet, exercising and medication in cardiovascular disease management.

A doctor reviewing the patient's risk factors can formulate an individual course of treatment, and the infomediary site 100 provides a list of possible treatments 908, including exercise, diet, pharmaceuticals, which are preferably customized by the CV Therapeutic database 906 in response to the risk factors identified by the test results of the patient. The physician sends an individualized treatment plan to a patient record in the infomediary site and the patient sends compliance information to the physician to the patient file. Either may access the relevant treatment plan records, but preferably only the physician may modify the recommended plan, and the patient may add, update or modify the compliance data.

The quantitative measurement of LDL and HDL lipid fractions and other lipid measurements are important patient data that is evaluated in the infomediary site. U.S. Pat. No. 5,925,229 describes methods for quantitating LDL fractions for evaluating cardiac disease risk and that patent is incorporated herein by reference. Typical lipids and their method for measurement are listed in Table I.

TABLE I

| Analysis | Methodology | Summary Description of Assay |
|---|---|---|
| Apoprotein A1 | Immuno-turbidimetric Analysis | An insoluble turbid immunoprecipitate is formed by the reaction between Apo A-1 antigen in human plasma and specific antibodies. Resulting turbidity is measured spectrophorometrically. Concentration of Apo A-1 is determined from a five-point calibration curve. Patients run in duplicate. |
| Apoprotein B | Immuno-turbidimetric Analysis | An insoluble turbid immunoprecipitate is formed by the reaction between Apo B antigen in human plasma and specific antibodies. Resulting turbidity is measured spectrophotometrically. Concentration of Apo B is determined from a five point calibration curve. Patients run in duplicate. |
| Apoprotein-E Isoforms | Isoelectric Focusing | Isoelectric focusing of plasma sample is followed histochemical visualization of the Apo-E bands. |
| Lipoprotein (a) | ELISA = Enzyme Linked Immuno-obsorbant Assay | Monoclonal/Polyclonal sandwich assay. Monoclonal antibody coated wells are used to capture Lp(a) from the sample. Polyclonal anti-Lp(a) horseradish peroxidase conjugate reacts with substrate and a chromogen producing colored solution. Concentration of Lp(a) mass (mg/dl) quantitatively determined by standard curve Patients run in duplicate: |
| Lipid Profile | | |
| Cholesterol | Enzymatic | Photometric quantification |
| Triglyceride | Enzymatic | Photometric quantification |
| HDL Cholesterol | Dextran & Magnesium sulfate | Precipitation of LDL and VLDL from plasma followed by assay of supernatant for cholesterol. |
| LDL Cholesterol | Calculated - Friedewald Formula | LDL = T Chol – HDL Chol – VLDL (Trig/5) |
| Homo-cysteine | FPIA = Fluorescence Polarization Immuno-assay | Specific monoclonal antibody detection with fluorescently labeled analog tracer detection. |

TABLE I-continued

| Analysis | Methodology | Summary Description of Assay |
|---|---|---|
| LDL GGE | Gradient Gel Electro- phoresis | Plasma low density lipoproteins (LDL) are characterized for particle size and distri- bution of lipid stained mass using poly- acrylamide gradient gels (2-14%). LDL particle size analysis is based on a four- point curve using lipoprotein standards correlated by analytical ultracentrifugation (ANUC). Results of phyenotype analysis are validated by comparison of GGE analysis with ANUC. |
| HDL GGE | Gradient Gel Electro- phoresis | Plasma high density lipoproteins (HDL) are characterized for particle size and distri- bution of protein stained mass using poly- acrylamide gradient gels (3-31%). HDL particle size analysis is based on calibration with globular protein standards. Results validated by comparison of GGE analysis with analytical ultracentrifugation (ANUC). |

Patient data from lipid analysis and other data have been utilized to develop a knowledge database within the infomediary site. This knowledge base is useful in analyzing an individual patient's data and also identifying new and previously unknown relationships between test results that aid in the diagnosis and treatment of patients. Additional relationships are identified from the tables 900, 902, and 904 using standard data mining techniques, including genetic algorithms, decision tree induction, association discovery, fuzzy logic, etc. The relationships are then incorporated into the CV therapeutic database 906. More particularly, the relationships may be incorporated into programs or scripts (e.g., SQL scripts) within the diagnostic engine 113.

Considering 954 patient samples (458 cases and 496 controls), age was a very significant predictor of CVD. Cases are significantly older than controls (60 vs. 52 years of age). After adjusting for the age difference, none of the risk factors are significantly different between the cases and controls. Thus, using the 954 patients, all of the differences in risk factors that exist between cases and controls are due to age, not disease status. All of these patients are high risk and the younger patients have not yet shown clinical manifestation of cardiovascular disease.

Using a subset of age matched cases (N=173, means 60 yr.) and controls (N=173, means 59 yr.) between 54 and 66 years of age, the cases had significantly:

Higher homocysteine (9.7 vs. 8.7, $P<0.01$), and

Lower TC (179 vs. 201, $p<0.0001$), LDLC (107 vs. 121, $p<0.001$), triglyceride (140 vs. 163, $p<0.05$), apoA1 (112 vs. 123, $p<0.01$) apoB (85 vs. 96, $p<0.001$), and TC/HDL2b (14.8 vs. 20.2, $p<0.05$). These data indicate that the cases are more aggressively treated with medications than the controls.

Using a subset of age-matched cases (N=146, mean 55 yr.) and controls (N=93, mean 55 yr.) between 44 and 66 years of age without hyperlipidemia, the cases had:

Higher HDL3b (19.9 vs. 17.9, $p<0.05$), HDL3 (58.8 vs. 55.7, $p=0.08$) and LDLII+IV/HDL2+3 (0.40 vs. 0.38, $p=0.11$), and Lower TC (182 vs. 205, $p<0.001$), LDLC (109 vs. 124, $p<0.01$), HDLC (44 vs. LDL11A (16.8 vs. 18.2, $p=0.09$), HDL2b (15.5 vs. 18.6, $p<0.05$), and HDL2 (41.3 vs. 44.5, $p=0.06$). These data again indicate that cases may be more aggressively treated with medications than the controls, even though they do not have hyperlipidemia. These data also indicate some important risk factors in the cases: a higher ratio of small LDL to HDL, small LDL size and lower HDL2b.

These data illustrate the value of the cardiovascular informatic knowledge base in deriving heretofore unrecognized relationships between data, especially highly discriminating lipoprotein subfractions, in diagnosing risk factors which may govern the treatment of patients.

Detailed Description of the Infomediary Site

In a preferred embodiment, the infomediary (information intermediary) site 100 is accessed over a network 101, either a public network such as the internet, or a private network such as a private LAN/WAN, either of which may be accessed over high speed digital subscriber lines or optional dial up (circuit switched) connections provided by a remote authentication server or the like. The network 101, as shown in FIG. 24, may include landline and/or wireless access (typically CDMA), as is known in the telecommunications art.

The healthcare information is typically displayed on a web browser running on a personal computer or other web-content viewing device. In the case of patient access, this may include a personal computer 107 with internet access, a television set with a set-top decoder (such as that provided by WorldGate™ Communications, Microsoft®'s WebTV®, service OpenTV® interactive television, or the like), and may also include a cable modem or wireless modem, or may be a smaller internet appliance device. The patient may also utilize tele-medicine devices such as a weight scale 115, blood pressure cuff 116, electrocardiogram device 117 or other similar monitoring devices.

In the case of a physician, any of the above access devices may be used. Preferably, physicians utilize a portable device such as a clipboard or tablet computer 107 such as those available from Fujitsu, a Clio® handheld device available from Vadem, or a smaller device such as a Palm® handheld device. The device may have wireless access 111 to the network for data transfers, or may store information locally on a computer 103 and periodically synchronize with the infomediary site via the network.

The information pages are conveyed to the browsing device over the network in the form of a device independent language such as hypertext markup language (html) using hypertext transfer protocol (http). These protocols are typically carried by a lower level transfer protocol such as those associated with the TCP/IP protocol suite. The device independent language is preferably generated dynamically by the infomediary site, using Common Gateway Interface (CGI) scripts, Active Server Pages (ASP), or other content generation languages and protocols. CGI and ASP are language-independent frameworks for coding of server-side scripts that are executed by Web server 112 in response to a user's request for a universal resource locator (URL). The infomediary site may also be accessible from an interactive television channel having regular multimedia displays of health-related educational information, documentaries, and the like, with the healthcare management features described herein being accessible to patients using software or scripts written in accordance with known interactive television transmission platforms and protocols, such as that provided by OpenTV®'s suite of EN2 set-top box software, software development tools, studio authoring tools, and Openstreamer data streaming software.

In response to user requests, the infomediary server scripts 112 access the database 104, which contains numerous data tables as shown in FIGS. 18-22. For example, ASP scripts provide database access via Microsoft®'s ActiveX Data Objects (ADO), which allows access to ODBC or OLEDB compliant data source including Microsoft® Access® (Jet), Microsoft® SQL Server, and Oracle® databases.

The data tables will now be described with reference to FIGS. 18-22. The various tables in FIGS. 18-22 make up a relational database, where the tables are related as indicated by the interconnecting lines. As is known to those of skill in the art, tables within relational databases may exhibit a one-to-many relationship. An exemplary description of such a relationship will be given with reference to the UserID of the TWebUsers table 800. The remaining tables are related in a similar manner as is apparent from the drawings.

Table 800 contains a record for each of the users of the infomediary site 100. Each UserID is a unique number defining a particular user's characteristics, including their login name, password, usertype, and a timestamp indicating when the record was created. The tables 801, 803, and 805, all include fields that are linked to the UserID within table 800. The key symbol at the end of the lines connected to table 800 indicate that the value within the UserID field specifies a unique record within the tWebUsers table 800, while the infinity symbol on the other end of the lines connected to tables 801, 803, and 805 indicate that more than one record in those tables can be linked to the same UserID in table 800. As is know to those of skill in the art, relating the tables in this manner results in a more efficient and powerful database structure than a single large data table.

Figure 20:
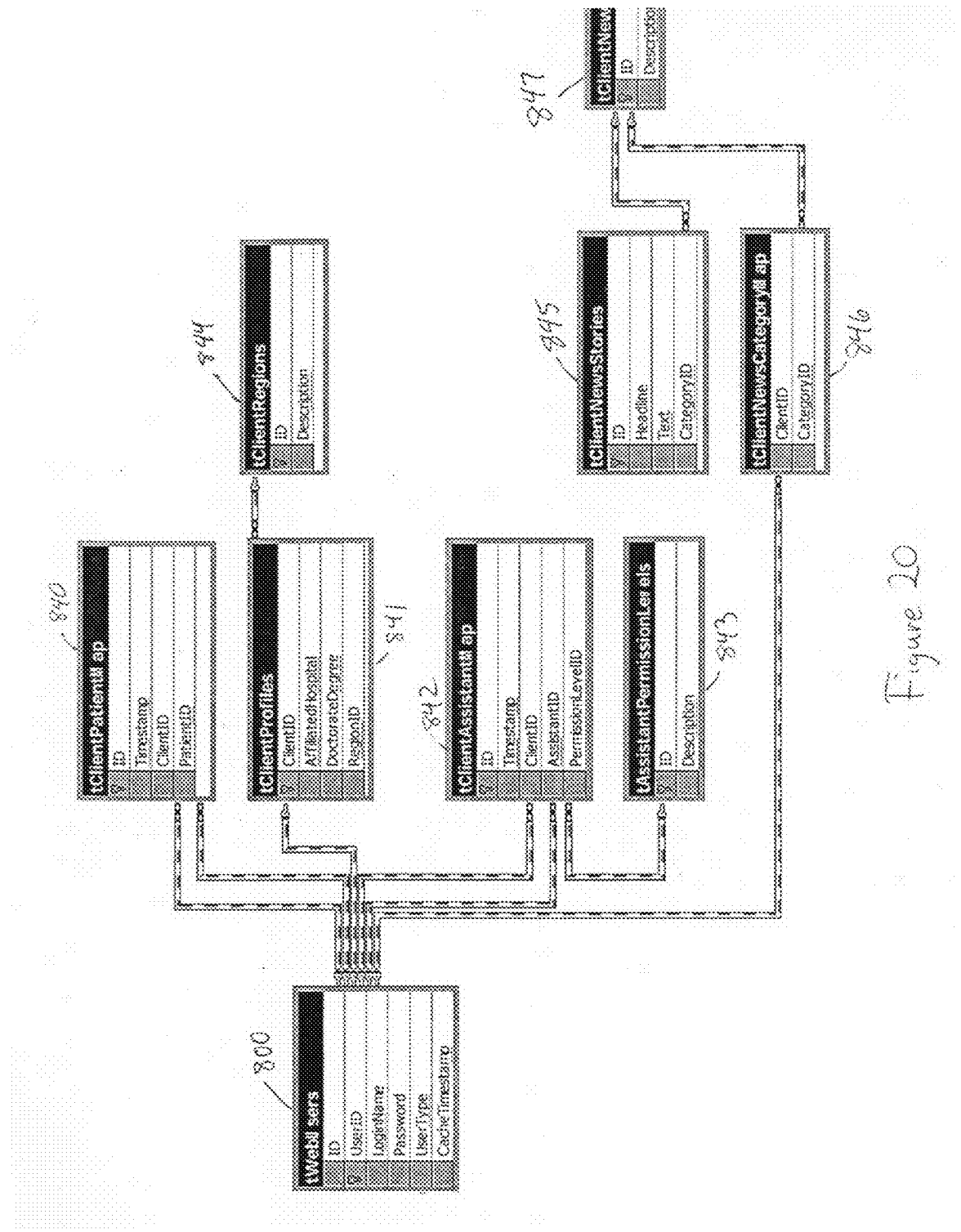

The table contents will now be generally described, in view of the above-defined relationships. When a patient initially registers with the infomediary site 100, he or she is associated with a physician. The registration is typically performed by the physician's office assistants (independently or with the aid of infomediary site personnel) in advance of the patient's first visit to the infomediary site. With reference to FIG. 20, client patient table 840 links a patient's webuser ID to the relevant physician webuser IDs. Table 841 links physicians (by the clientID) to a physician profile including an affiliated hospital, degree, and region (further described in client region table 844). As shown in client assistant map table 842, each physician assistant has an assistant ID, a clientID (i.e., physician), and a permission level (as described in permission level table 843). Physicians may be categorized according to client category map table 846 (as described by client news category table 847, and news stories may be categorized as shown in table 845.

Figure 18:
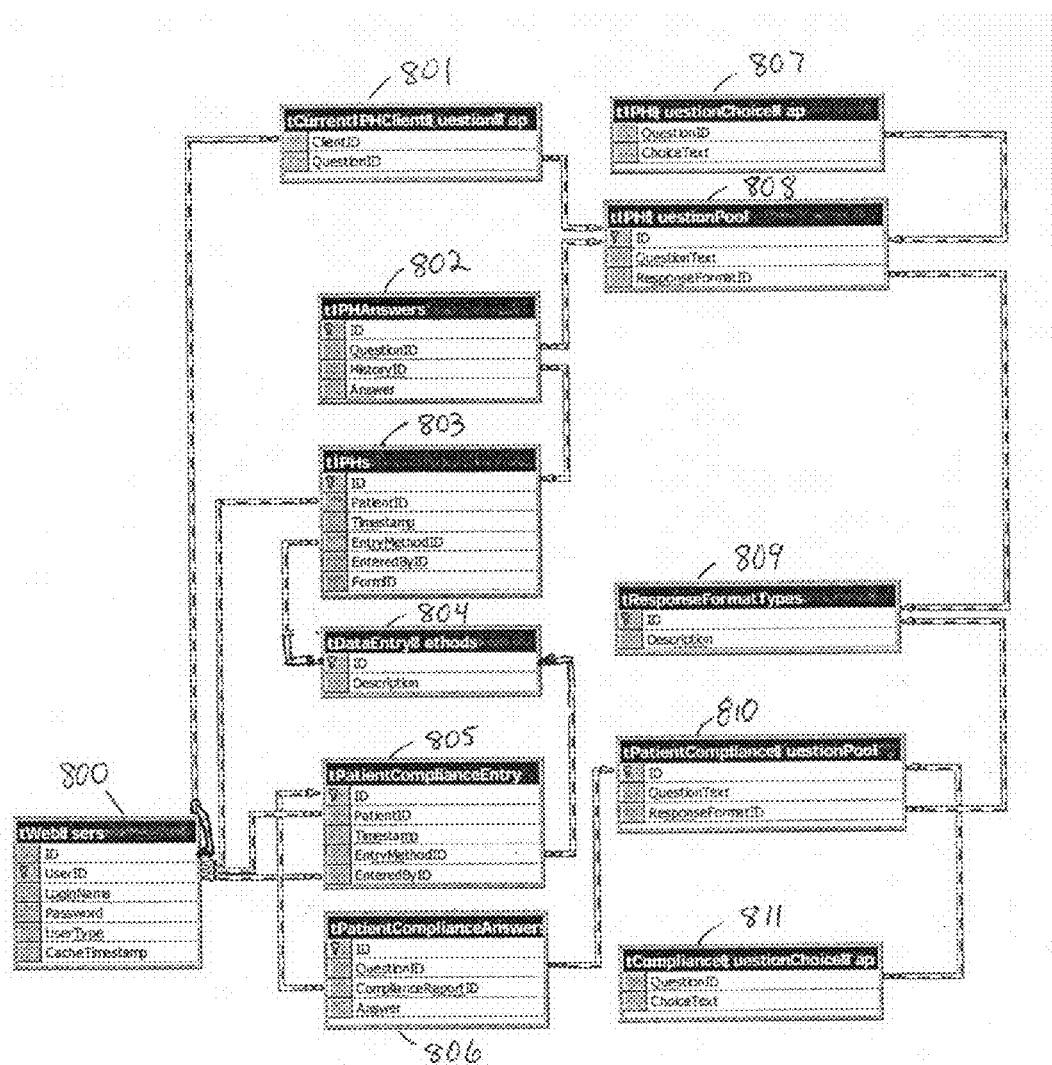
FIGS. 18-22 show the database tables of the preferred embodiment.

With reference to FIG. 18, tables 801, 802, 803, 804, 807 and 808 are used to gather the patient history data. Either the patient or data entry personnel (such as a physician's assistant or a case manager or technician provided by the infomediary site) using an appropriate interface (preferably a GUI, such as a web browser, or another database entry interface) collects data that is inserted into the tables. The tables are preferably accessed using a data entry interface such as the web pages provided by the web server 112. When the patient or data entry personnel navigate to the relevant input screens, the database management system 115 (or server scripts 112, such as ASP server scripts) queries the question map table 801 to determine which questions the physician wishes to ask his patients. Each physician (identified by the ClientID field in table 801, which is in turn linked to a UserID in table 800) may create a customized list of questions from a question pool. The list of questions is stored as individual records in table 801 corresponding to that physician. The questionIDs are used to retrieve the question text and response format from question pool table 808. The description of the response format is then obtained from table 809, and the question is presented to the patient. If the patient is accessing the site directly, the questions are preferably presented in the form of web pages to the patient. If data entry personnel are utilized, the question may be read to the patient to solicit the response. The responses are entered and submitted to the database system, and are stored in tables 802 and 803. Tables 804, 805, 806, 809, 810 and 811 are used in a similar to gather compliance information.

Figure 19:
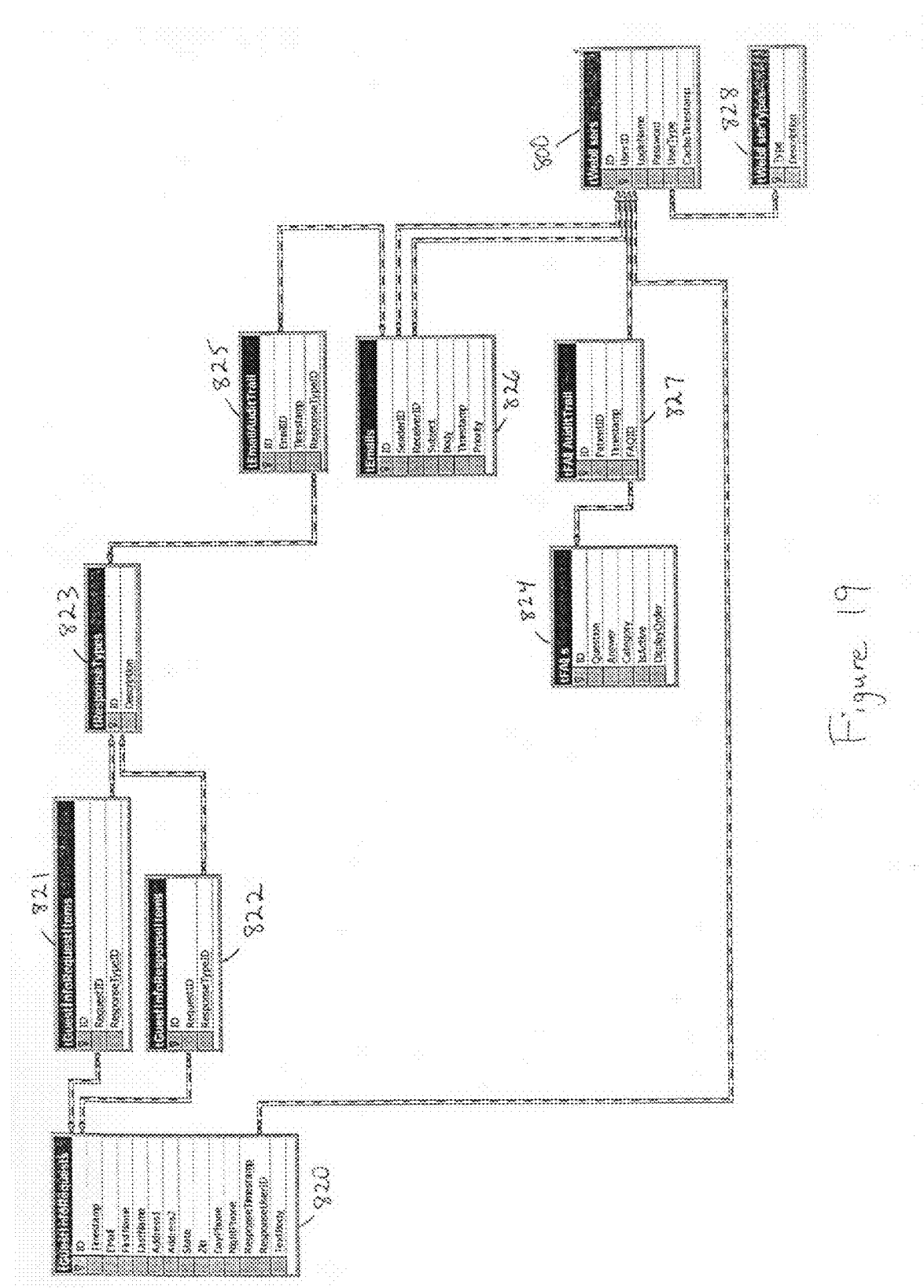

With reference to FIG. 19, tables 820, 821 and 822 are used to gather guest information, including requests for information and contact information. Tables 825 and 826 are used to provide a communication interface that facilitates communication between physicians and patients. The sender and receiver are identified, along with the subject, body, date, time and priority, etc. Thus, when a physician logs in and requests to view his email, the communication interface, preferably made up of server scripts and database management software, queries email table 826 for all entries having the physician's UserID (table 800) in either the senderID or receiverID field. Those entries may be looked up in email audit table 825 to check the status.

Figure 21:
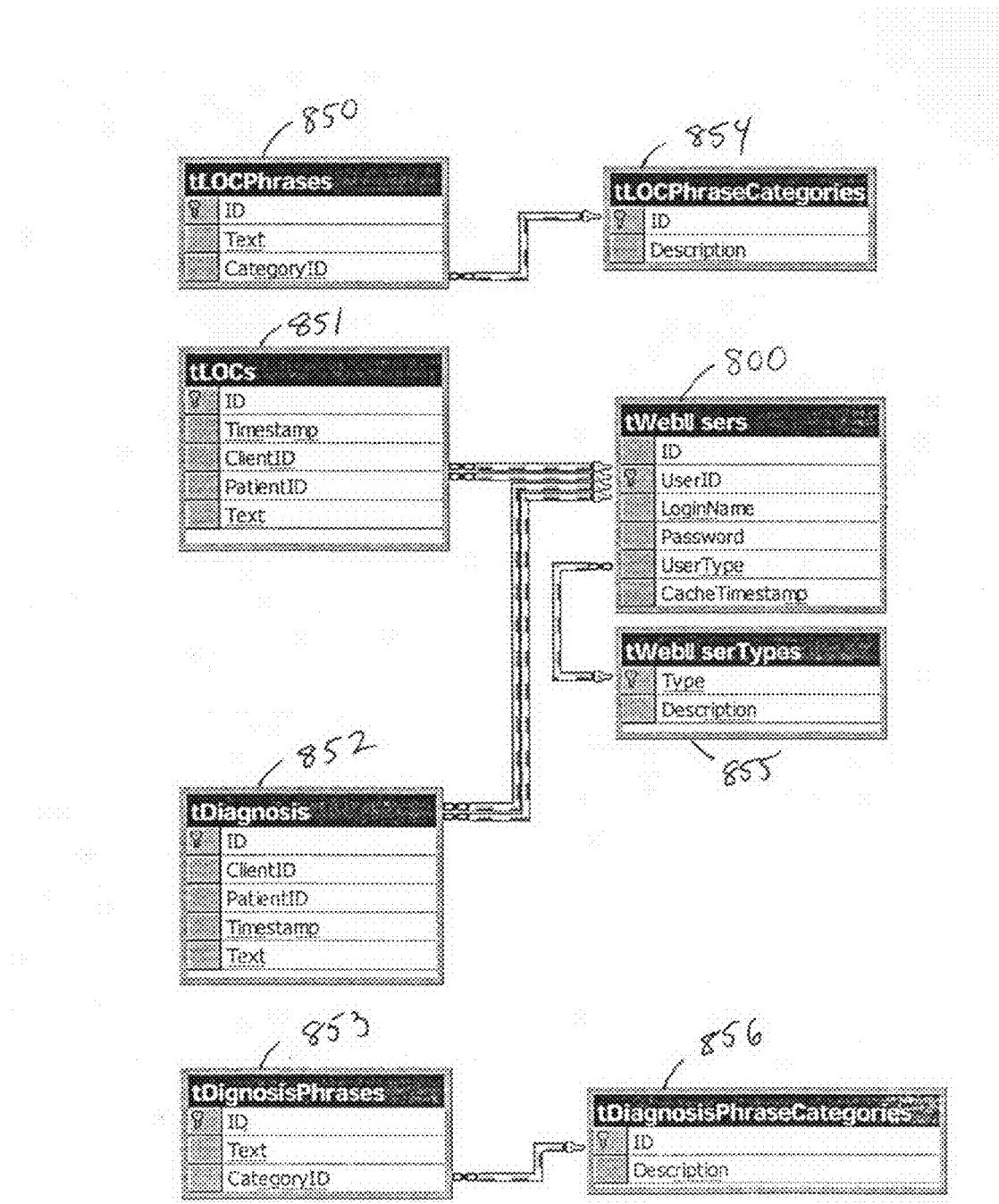

Table 827 keeps a log of frequently asked questions (FAQs—as stored in FAQ table 824) that have been accessed by a given patient, thus allowing a physician to obtain further information about potential concerns of his or her patients. With reference to FIG. 21, Letters of consultation may be created using tables 850, 851 and 854. New diagnoses are created via the physician data access interface and stored in table 852. The template for creating a diagnosis may be created using standard diagnostic phrases obtained from tables 853 and 856. The new diagnosis template may present the cardiologist with certain diagnosis suggestions based on the test results. Specifically, the diagnostic 113 engine may perform algorithmic tests on new test results and store one or more diagnosis candidates in diagnosis fields (not shown) in the test results table 902.

Figure 22:
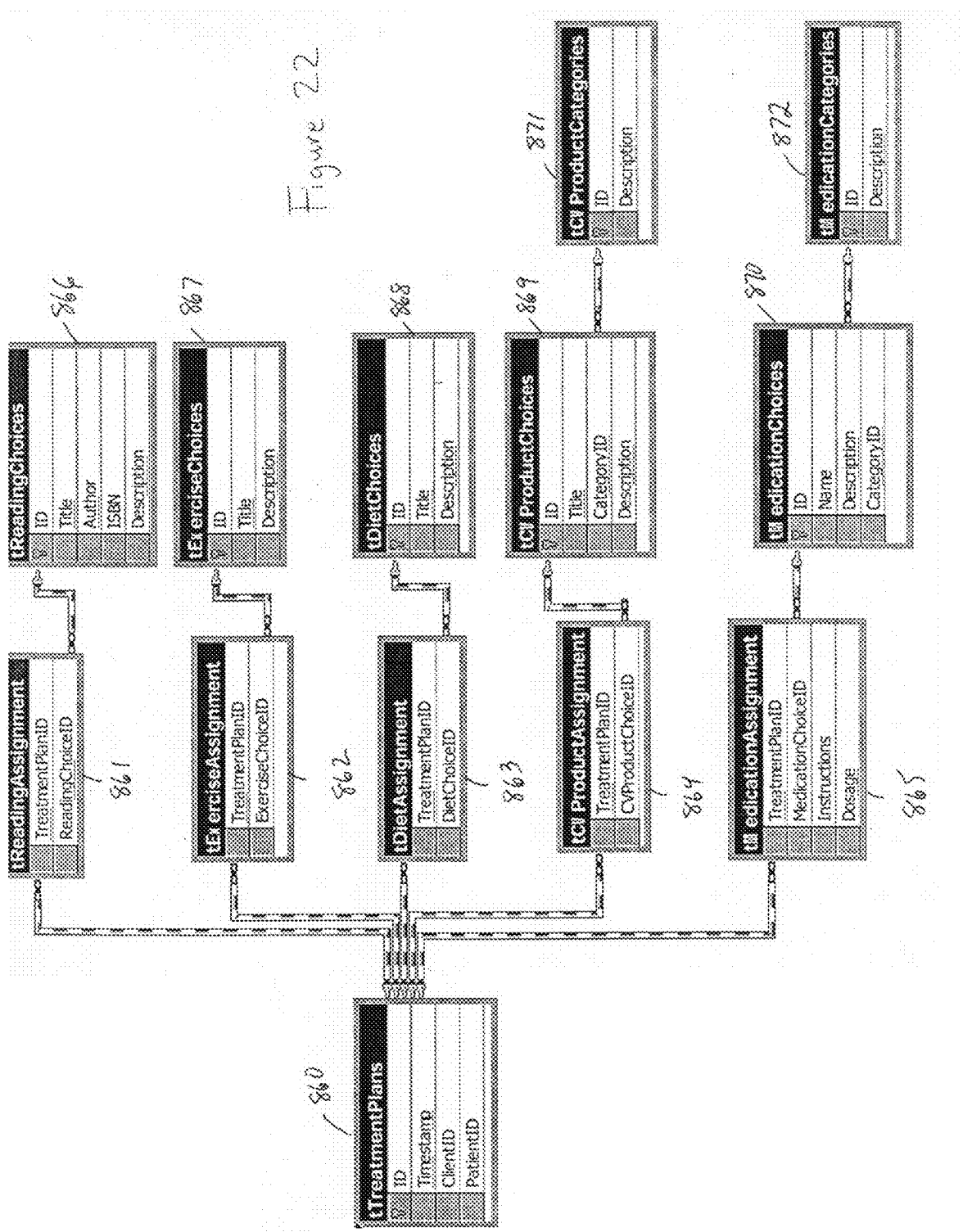

With reference to FIG. 22 treatment plans are stored in tables 860-865. Physicians, through the physician data access interface, create treatment plans for individual patients. Typically, the treatment plan is created or updated after test results become available. The treatment plan template is preferably generated and stored in treatment plan table 860, reading assignment table 861, Exercise assignment table 862 diet assignment table 863, CV product assignment table 864, and education assignment table 865. Tables 866, 867; 868, 869, 870, 871 and 872 are used to store possible selections for the corresponding tables as shown in FIG. 22. When a treatment plan template is generated for the physician, the diagnostic engine may be utilized to query Diagnosis table 852 and responsively determine suggested treatment plan components to be displayed as a suggested treatment plan within the template.

The diagnostic engine may also query relevant test result tables, patient history tables, compliance tables and the like to determine the suggested treatment plan. Prior to the cardiologist's review of the suggested treatment plan, the case manager or physician's assistant may initially access it to review it. The case manager may modify the plan or accept it and submit it to the cardiologist for final approval and posting to the patient's folder where the patient may view the plan.

With respect to FIG. 25, the flow chart for the method 1000 will be described. At step 1002 the test result data is stored. As described herein, the test data may be received over a network from a lab. At step 1004 the test result data is supplied to the physician. Preferably, the test data is provided using web pages conveyed over a network. At step 1006 the site receives diagnostic data from the physician. The diagnostic data is stored in the database as part of the patient's record. At step 1010 the site receives treatment plan information from the physician. The treatment plan is likewise stored in the patient's record. At step 1012 the site provides treatment plan information to the patient, also via web pages conveyed over a network.

With respect to FIG. 26, the flow chart for the method 1100 will be described. Steps having the same number as in the method 1000 are essentially the same. However, the method 1100 includes additional steps. At step 1003 the test result data is analyzed. The analysis is preferably performed using diagnostic engine 113. The diagnostic analysis information is stored in a table and associated with the relevant test results. The diagnostic analysis data is preferably one or more suggested diagnoses based upon the test results and other salient data from the clinical database 105 and information database 104. At step 1005 the test result data and the diagnostic data is supplied to the physician. At step 1007 the site analyzes the diagnostic data received from the physician. The analysis preferably identifies possible treatment plan information, including possible prescriptions, diets, exercises, CV products, educational materials, etc., as discussed above. It should be noted that information identified as being provided to and received from the physician may actually be submitted and received by a physician's assistant, nurse, or other responsible party. The term physician is used in this context to refer to the fact that the submission of diagnosis and treatment plans should be performed under the supervision of a physician.

A preferred embodiment of the present invention has been described herein. It is to be understood, of course, that changes and modifications may be made in the embodiment without departing from the true scope of the present invention, as defined by the appended claims. The present embodiment preferably includes logic to implement the described methods in software modules as a set of computer executable software instructions. The Computer Processing Unit ("CPU") or microprocessor implements the logic that controls the operation of the site, diagnostic engine, and database. The microprocessor executes software that can be programmed by those of skill in the art to provide the described functionality.

The software can be represented as a sequence of binary bits maintained on a computer readable medium including magnetic disks, optical disks, and any other volatile or (e.g., Random Access memory ("RAM")) non-volatile firmware (e.g., Read Only Memory ("ROM")) storage system readable by the CPU. The memory locations where data bits are maintained also include physical locations that have particular electrical, magnetic, optical, or organic properties corresponding to the stored data bits. The software instructions are executed as data bits by the CPU with a memory system causing a transformation of the electrical signal representation, and the maintenance of data bits at memory locations in the memory system to thereby reconfigure or otherwise alter the unit's operation. The executable software code may implement, for example, the methods as described above.

It should be understood that the programs, processes, methods and apparatus described herein are not related or limited to any particular type of computer or network apparatus (hardware or software), unless indicated otherwise. Various types of general purpose or specialized computer apparatus may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

It should be understood that a hardware embodiment may take a variety of different forms. The hardware may be implemented as one or more server computers. For example, the web server may reside on one computing platform that accesses the database system residing on another computing platform.

The claims should not be read as limited to the described order of elements unless stated to that effect. In addition, use of the term "means" in any claim is intended to invoke 35 U.S.C. § 112, paragraph 6, and any claim without the word "means" is not so intended. Therefore, all embodiments that come within the scope and spirit of the following claims and equivalents thereto are claimed as the invention.

What is claimed is:

1. A cardiovascular healthcare management system comprising:
    (a) an infomediary site having databases for cardiovascular healthcare management which includes a database of test results of concentration of subclasses of LDL particles and subclasses of HDL particles from at least 900 cardiovascular patients;
    (b) a data entry interface for receiving patient personal data and test results for concentration of subclasses of LDL particles and subclasses of HDL particles storing the data and results in the infomediary site databases;
    (c) a diagnostic engine comprising algorithms stored on a computer-readable medium and executed by a microprocessor for analyzing patient test results for subclasses of LDL particles, subclasses of HDL particles data and identifying patients who do not have hyperlipidemia based on total LDL cholesterol and total HDL cholesterol, but are in need of treatment; and
    (d) wherein the subclasses of LDL particles and subclasses of HDL particles are levels determined by segmented gradient gel electrophoresis and wherein the particle sub-classes include HDL 2b.

2. The cardiovascular healthcare management system of claim 1 further comprising a physician data access interface to allow physician access to the infomediary databases.

3. The cardiovascular healthcare management system of claim 1 further comprising a communication system allowing the physician to communicate cardiovascular healthcare management information to the patient.

4. The cardiovascular healthcare management system of claim 1 further comprising a cardiovascular knowledge base that stores information related to cardiovascular risk factors.

5. The cardiovascular healthcare management system of claim 1 wherein the diagnostic engine includes algorithms for associating test results with possible treatments.

6. The cardiovascular healthcare management system of claim 1 wherein the diagnostic engine includes algorithms for associating test results with possible diagnoses.

7. The cardiovascular healthcare management system of claim 1 wherein the diagnostic engine includes algorithms for associating diagnosis information with possible treatment plans.

8. The cardiovascular healthcare management system of claim 7 wherein the treatment plans include personalized drugs, diet and exercise suggestions.

* * * * *